US011355238B2

(12) United States Patent
Kovatchev

(10) Patent No.: US 11,355,238 B2
(45) Date of Patent: Jun. 7, 2022

(54) METHOD, SYSTEM AND COMPUTER PROGRAM PRODUCT FOR EVALUATION OF BLOOD GLUCOSE VARIABILITY IN DIABETES FROM SELF-MONITORING DATA

(75) Inventor: Boris P. Kovatchev, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 2523 days.

(21) Appl. No.: 12/159,891

(22) PCT Filed: Jan. 5, 2007

(86) PCT No.: PCT/US2007/000370
§ 371 (c)(1),
(2), (4) Date: Sep. 10, 2008

(87) PCT Pub. No.: WO2007/081853
PCT Pub. Date: Jul. 19, 2007

(65) Prior Publication Data
US 2009/0171589 A1 Jul. 2, 2009

Related U.S. Application Data

(60) Provisional application No. 60/756,340, filed on Jan. 5, 2006, provisional application No. 60/786,944, filed on Mar. 29, 2006.

(51) Int. Cl.
*G16H 50/20* (2018.01)

(52) U.S. Cl.
CPC .................. *G16H 50/20* (2018.01)

(58) Field of Classification Search
CPC ..... A61B 5/14532; A61B 5/746; A61B 5/742; A61B 5/7275; A61B 5/7221; A61B 5/4866; A61B 5/7203; A61B 5/7239; A61B 5/7257; A61B 5/726; A61B 5/486; A61B 5/145; A61B 5/7475; A61B 5/7264; A61B 5/743; A61B 5/4839; A61B 5/7267; A61B 2560/0223; A61B 5/4842; A61B 5/14503; A61B 5/7405; A61B 5/4848; A61B 5/7271; A61B 5/7278; A61B 5/7282; A61B 5/7285; A61B 5/7296; A61B 5/74; G06F 19/00; G06F 19/3468; G06F 17/10; G06F 19/34; G06F 3/04817; G06F 17/18; G06F 17/12; G16H 40/63; G16H 50/30; G16H 50/50; G16H 10/60; G16H 50/20; G16H 40/67; G16H 20/17; G16H 20/10; G16H 15/00; G16H 20/60; G16H 40/60; G16H 20/13; G16H 10/40; G16H 50/70; G16H 10/20; G16H 70/20; G16H 70/40; G16H 40/40; G16H 20/00; G01N 33/66; G01N 2800/042; G01N 2800/52; G01N 33/50; G01N 2800/50; G01N 33/48707; G01N 33/48721; G01N 33/48; G01N 33/48792; Y02A 90/26; A61P 3/10; A61P 3/08; A61M 5/1723; A61M 2230/201; A61M 2205/50; A61M 2205/52; A61M 2205/18; A61M 2205/502; A61M 2005/1726; A61M 5/142; A61M 5/14; A61M 5/14244; A61M 2005/14208; A61M 2005/2093; A61M 2205/581; A61M 2230/005; G08B 21/0453; G06K 9/00496; G06K 9/6215; G06K 9/6218; G16B 40/00; G16B 99/00; G16B 5/00; G16B 20/00; G16B 20/20; G16B 20/10; G16B 40/30; G06N 20/00; G06N 5/043; G06N 5/047; G06N 7/005; G01R 33/465; A61K 38/28; C12Q 2600/118

See application file for complete search history.

(56) References Cited

U.S. PATENT DOCUMENTS

| 4,695,954 A | 9/1987 | Rose et al. |
| 4,731,726 A | 3/1988 | Allen, III |
| 4,779,199 A | 10/1988 | Yoneda et al. |

(Continued)

FOREIGN PATENT DOCUMENTS

| EP | 0 462 466 B1 | 12/1991 |
| JP | 5292104 B2 | 9/2013 |

(Continued)

OTHER PUBLICATIONS

Kovatchev at al. (Diabetes Care, 1997, 20(11), 1655-1658).*

(Continued)

*Primary Examiner* — Mary K Zeman
(74) *Attorney, Agent, or Firm* — Potomac Law Group, PLLC; Vincent M DeLuca; Robert J. Decker

(57) ABSTRACT

A system, computer program product, method and algorithm for evaluation of blood glucose variability—one of the most important parameters of diabetes management. An embodiment of the method may use routine self-monitoring blood glucose (SMBG) data collected over a period of 2-6 weeks, for example, based on a theory of risk analysis of blood glucose data. One aspect may include a method, system and computer program product for computing the Average Daily Risk Range (ADRR)—a measure of overall glucose variability. Another aspect may include a method, system, and computer program product for estimating separately the glucose variability in the hypoglycemic range via a Low BG Index (LBGI) and the glucose variability in the high BG range via High BG Index (HBGI) followed by a combination of the two indices into a single variability display.

66 Claims, 9 Drawing Sheets

(56) References Cited

U.S. PATENT DOCUMENTS

| | | |
|---|---|---|
| 4,817,044 A | 3/1989 | Ogren |
| 5,019,974 A | 5/1991 | Beckers |
| 5,216,597 A | 6/1993 | Beckers |
| 5,251,126 A | 10/1993 | Kahn et al. |
| 5,307,263 A | 4/1994 | Brown |
| 5,319,363 A | 6/1994 | Welch et al. |
| 5,341,291 A | 8/1994 | Roizen et al. |
| 5,376,070 A | 12/1994 | Purvis et al. |
| 5,500,854 A | 3/1996 | Uotila |
| 5,558,638 A | 9/1996 | Evers et al. |
| 5,590,648 A | 1/1997 | Mitchell et al. |
| 5,626,144 A | 5/1997 | Tacklind et al. |
| 5,704,366 A | 1/1998 | Tacklind et al. |
| 5,713,856 A | 2/1998 | Eggers et al. |
| 5,772,586 A | 6/1998 | Heinonen et al. |
| 5,878,384 A | 3/1999 | Johnson et al. |
| 5,925,021 A | 7/1999 | Castellano et al. |
| 5,946,659 A | 8/1999 | Lancelot et al. |
| 5,960,403 A | 9/1999 | Brown |
| 5,974,389 A | 10/1999 | Clark et al. |
| 5,997,476 A | 12/1999 | Brown |
| 6,022,315 A | 2/2000 | Iliff |
| 6,024,699 A | 2/2000 | Surwit et al. |
| 6,049,764 A | 4/2000 | Stahl |
| 6,081,786 A | 6/2000 | Barry et al. |
| 6,134,504 A | 10/2000 | Douglas et al. |
| 6,144,922 A | 11/2000 | Douglas et al. |
| 6,188,988 B1 | 2/2001 | Barry et al. |
| 6,206,829 B1 | 3/2001 | Iliff |
| 6,225,901 B1 | 5/2001 | Kail, IV |
| 6,234,964 B1 | 5/2001 | Iliff |
| 6,270,455 B1 | 8/2001 | Brown |
| 6,277,071 B1 | 8/2001 | Hennessy et al. |
| 6,336,900 B1 | 1/2002 | Alleckson et al. |
| 6,338,713 B1 | 1/2002 | Chamoun et al. |
| 6,352,505 B1 | 3/2002 | Bortz |
| 6,368,273 B1 | 4/2002 | Brown |
| 6,379,301 B1 | 4/2002 | Worthington et al. |
| 6,406,426 B1 | 6/2002 | Reuss et al. |
| 6,418,346 B1 | 7/2002 | Nelson et al. |
| 6,422,061 B1 | 7/2002 | Sunshine et al. |
| 6,450,956 B1 | 9/2002 | Rappaport et al. |
| 6,505,059 B1* | 1/2003 | Kollias ............... A61B 5/0071 600/316 |
| 6,524,240 B1 | 2/2003 | Thede |
| 6,540,672 B1 | 4/2003 | Simonsen et al. |
| 6,544,174 B2 | 4/2003 | West et al. |
| 6,544,212 B2 | 4/2003 | Galley et al. |
| 6,551,243 B2 | 4/2003 | Bocionek et al. |
| 6,558,321 B1* | 5/2003 | Burd ............... A61B 5/0022 600/300 |
| 6,558,351 B1 | 5/2003 | Steil et al. |
| 6,575,900 B1 | 6/2003 | Zweig et al. |
| 6,579,231 B1 | 6/2003 | Phipps et al. |
| 6,604,050 B2 | 8/2003 | Trippel et al. |
| 6,611,846 B1 | 8/2003 | Stoodley |
| 6,635,016 B2 | 10/2003 | Finkelshteins |
| 6,645,142 B2 | 11/2003 | Braig et al. |
| 6,656,114 B1 | 12/2003 | Poulsen et al. |
| 6,692,436 B1 | 2/2004 | Bluth et al. |
| 6,781,522 B2 | 8/2004 | Sleva et al. |
| 6,799,149 B2 | 9/2004 | Hartlaub |
| 6,804,558 B2 | 10/2004 | Haller et al. |
| 6,872,200 B2 | 3/2005 | Mann et al. |
| 6,915,170 B2 | 7/2005 | Engleson et al. |
| 10,431,342 B2* | 10/2019 | Kovatchev ............... G06F 19/00 |
| 2002/0016534 A1* | 2/2002 | Trepagnier ......... A61B 5/14532 600/316 |
| 2002/0026111 A1* | 2/2002 | Ackerman ........... A61B 5/1486 600/347 |
| 2003/0100821 A1* | 5/2003 | Heller ................. A61B 5/0002 600/347 |
| 2003/0191376 A1* | 10/2003 | Samuels ................ A61B 5/157 600/309 |
| 2003/0212317 A1* | 11/2003 | Kovatchev ............. G16H 50/50 600/365 |
| 2003/0216628 A1 | 11/2003 | Bortz et al. |
| 2005/0027182 A1* | 2/2005 | Siddiqui ................ G16H 40/67 600/365 |
| 2005/0027462 A1* | 2/2005 | Goode ............... A61B 5/14532 702/22 |
| 2005/0038332 A1* | 2/2005 | Saidara ................ A61B 5/0002 600/347 |
| 2005/0187789 A1 | 8/2005 | Hatlestad et al. |
| 2005/0209515 A1 | 9/2005 | Hockersmith et al. |
| 2005/0214892 A1* | 9/2005 | Kovatchev ......... A61B 5/14546 435/25 |
| 2005/0256384 A1* | 11/2005 | Walker ................. A61B 5/1455 600/316 |
| 2005/0267780 A1 | 12/2005 | Ray et al. |
| 2006/0010098 A1 | 1/2006 | Goodnow et al. |
| 2006/0106644 A1 | 5/2006 | Koo et al. |
| 2006/0173260 A1 | 8/2006 | Gaoni et al. |
| 2006/0189863 A1 | 8/2006 | Peyser et al. |
| 2007/0033074 A1 | 2/2007 | Nitzan et al. |
| 2009/0171589 A1 | 7/2009 | Kovatchev |

FOREIGN PATENT DOCUMENTS

| | | |
|---|---|---|
| WO | 01/72208 A2 | 10/2001 |
| WO | 2004/015539 A2 | 2/2004 |
| WO | 2007081853 A3 | 11/2007 |

OTHER PUBLICATIONS

Hirsch et al., "Should Minimal Blood Glucose Variability Become The Gold Standard of Glycemic Control?," Journal of Diabetes Complications, Jun. 2005, 19(3): pp. 178-181.

Service et al., "The Relation of Glycemia to the Risk of Development and Progression of Retinopathy in the Diabetic Control and Complications Trial," Diabetologia, Mar. 2001, 44(3): pp. 1215-1220.

Kovatchev et al., "Risk analysis of blood glucose data: A quantitative approach to optimizing the control of Insulin Dependent Diabetes," Journal of Theoretical Medicine, Jan. 1, 2000, pp. 1-10, vol. 3, No. 1. Taylor & Francis Ltd., United Kingdom.

F. John Service, M.D., et al., "Mean Amplitude of Glycemic Excursions, a Measure of Diabetic Instability", Diabetes, vol. 19, No. 9, Sep. 1970, pp. 644-655.

J. Schlichtkrull et al., "The M-Value, an Index of Blood-sugar Control in Diabetics", Acta Medica Scandinavica, vol. 177, fasc. 1, 1965, pp. 95-102.

David Rodbard, M.D., "Optimizing Display Analysis, Interpretation and Utility of Self-Monitoring of Blood Glucose (SMBG) Data for Management of Patients with Diabetes", Journal of Diabetes Science and Technology, vol. 1, Issue 1, Jan. 2007, pp. 62-71.

Accu-Check Camit Pro User's Manual, Roche Diagnostics, 2005, 220 pages.

Edmond A. Ryan et al. "Assessment of the Severity of Hypoglycemia and Glycemic Lability in Type 1 Diabetic Subjects Undergoing Islet Transplantation", , Diabetes, vol. 53, Apr. 2004, pp. 955-962.

Boris P. Kovatchev et al., "Evaluation of a New Measure of Blood Glucose Variability in Diabetes", Diabetes Care, vol. 29, No. 11, Nov. 2006, pp. 2433-2438.

Michael Brownlee, MD et al., "Glycemic Variabiity: A Hemoglobin $A_{1c}$-Independent Risk Factor for Diabetic Complications", (reprinted) JAMA, vol. 295, No. 14, Apr. 12, 2006, pp. 1707-1708.

Irl B. Hirsch, M.D. "Glycemic Variability: It's Not Just about A1C Anymore!", Diabetes Technology & Therapeutics, 2005, pp. 780-783, vol. 7, No. 5.

Boris P. Kovatchev, et al., Methods for Quantifying Self-Monitoring Blood Glucose Profiles Exemplified by an Examination of Blood Glucose Patterns in Patients with Type 1 and Type 2 Diabetes Technology & Therapeutics, 2002, pp. 295-303, vol. 4, No. 3.

Louis Monnier et al., "Activation of Oxidative Stress by Acute Glucose Fluctuations Compared with Sustained Chronic Hyperglycemia in Patients with Type 2 Diabetes", JAMA, Apr. 12, 2006, pp. 1681-1687, vol. 295, No. 14.

(56) References Cited

OTHER PUBLICATIONS

David Rodbard, "Improved Methods for Calculating a Figure of Merit for Blood Glucose Monitoring Data", Diabetes Technology Meeting, San Francisco, CA, Nov. 2005, 1 page.

J.M. Wojcicki, ""J"-Index. A New Proposition of the Assessment of Current Glucose Control in Diabetic Patients", Hormone and Metabolic Research, 1995, pp. 41-42, vol. 27.

Russian Decision of Grant dated Sep. 28, 2012, in corresponding Russian application.

Kovatchev et al.; "Quantifying Temporal Glucose Variability in Diabetes via Continuous Glucose Monitoring Mathematical Methods and Clinical Application"; vol. 7; No. 6; 2005; pp. 849-862.

\* cited by examiner

METHOD, SYSTEM AND COMPUTER PROGRAM PRODUCT FOR EVALUATION OF BLOOD GLUCOSE VARIABILITY IN DIABETES FROM SELF-MONITORING DATA

RELATED APPLICATIONS

The present patent application claims priority from U.S. Provisional Application Ser. No. 60/756,340, filed Jan. 5, 2006, entitled "Method, System and Computer Program Product for Evaluation of Blood Glucose Variability in Diabetes from Self-Monitoring Data," and No. 60/786,944, filed Mar. 29, 2006, entitled "Method, System and Computer Program Product for Evaluation of Blood Glucose Variability in Diabetes from Self-Monitoring Data," the entire disclosures of which are hereby incorporated by reference herein.

GOVERNMENT SUPPORT

Work described herein was supported by Federal Grant No. R01 DK51562, awarded by NIH. The Government has certain rights in the invention.

TECHNICAL FIELD OF INVENTION

The present system relates generally to the art of glucose monitoring, and more particularly to hypo- and hyperglycemic risk assessment.

BACKGROUND OF INVENTION

The Importance of Controlling Blood Glucose Variability in Diabetes

Diabetes is a complex of disorders, characterized by a common final element of hyperglycemia, that arise from, and are determined in their progress by mechanisms acting at all levels of bio-system organization—from molecular to human behavior. Diabetes mellitus has two major types: Type 1 (T1DM) caused by autoimmune destruction of insulin producing pancreatic beta-cells, and Type 2 (T2DM), caused by defective insulin action (insulin resistance) combined with progressive loss of insulin secretion. Twenty million people are currently afflicted by diabetes in the US, with epidemic increases now occurring. The risks and costs of diabetes (over $100 billion/yr) come from its chronic complications in 4 major areas: retinal disease which is the leading cause of adult blindness, renal disease representing half of all kidney failures, neuropathy which predisposes to over 82,000 amputations each year, and cardiovascular disease (CVD), which is 2-4 times more common than in those without diabetes. Cardiovascular disease in diabetes is also more morbid, more lethal and less benefited by modern interventions such as bypass surgery or stents. On a positive note, intensive treatment with insulin and/or oral medications markedly reduces most complications in both T1DM (60) and T2DM (62), including cardiovascular disease (27). The, now classic, DIGAMI study confirmed the benefits of strict metabolic management for patients with diabetes who were suspected of having acute myocardial infarction (24). The follow-up of this study, DIGAMI-2 (51), confirmed the important benefits of aggressive metabolic management, showing that in well-controlled diabetes cardiovascular outcomes are similar to those in a nondiabetic population.

Glycosylated hemoglobin ($HbA_{1c}$) is the classic marker of glycemic status, introduced 23 years ago (1), linked to long-term complications of diabetes, and confirmed as the gold standard for both T1DM and T2DM (56). Contemporary studies, however, increasingly concentrate on the variability of blood glucose (BG) fluctuations, specifically on its two most important extreme manifestations: hypoglycemia, and postprandial glucose (PPG) excursions into hyperglycemia.

Hypoglycemia is common in T1DM (61) and becomes more prevalent in T2DM with treatment intensification (36). Consequently, hypoglycemia has been identified as the primary barrier to optimal diabetes management (15,16,18,19). The evaluation of risk for hypoglycemia has been variably accurate and generally limited to evaluation of long-term risk trends: In the Diabetes Control and Complications Trial (DCCT) about 8% of the variance of future severe hypoglycemic (SH) episodes could be accounted for from known variables, including $HbA_{1c}$ (60). A structural equation model using history of SH, $HbA_{1c}$, hypoglycemia awareness, and an autonomic score accounted for 18% of the variance in future SH (29). In a series of previous publications we reported that the Low Blood Glucose Index (LBGI, explained in the Methods section) accounted for 40-55% of future (within 3-6 months) SH episodes, and history of SH could add an additional 5% to that long-term prediction (12,42,45). Many studies have established relationships between hypoglycemia, intensive insulin therapy, unawareness and impaired counterregulation (3,4,17,68) and concluded that hypoglycemia may lead to a "vicious cycle" of recurrent hypoglycemic episodes (18). According to the concept of hypoglycemia-associated autonomic failure (HAAF, 20), recent antecedent hypoglycemia causes defective counterregulation and hypoglycemic unawareness. HAAF was observed in both T1DM (20) and advanced T2DM (58). Considering this extensive research, it is reasonable to expect that SH episodes may be occurring with higher frequency during periods of increased BG variability that may be recognizable from self-monitored blood glucose (SMBG) data. In fact, we have reported observing 48-hour periods of increased glycemic variability that preceded and followed SH (39).

At the hyperglycemic end of the BG scale, in non-diabetic individuals PPG fluctuations are limited in both their peak value, rarely exceeding 140 mg/dl, and in their duration with a peak PPG at approximately 1 hour after the start of a meal and return to preprandial levels within 2-3 hours (2). In individuals with diabetes a number of factors, such as insulin resistance, inadequate available insulin, delayed insulin action, or abnormalities in glucagon secretion, contribute to delayed peak PPG, and higher and prolonged PPG elevation (2). Such abnormal glucose patterns lead to profound acute and chronic negative consequences that are expressed at all levels of the living organism—from microvascular complications, through heart disease, to aberrations in human behavior. Specifically, at the physiological level, a number of studies found that postprandial hyperglycemia is an independent factor contributing to CVD and increased mortality, especially in people with T2DM (28,31,32,33,35). New clinical trials continue to support the notion that postprandial hyperglycemia is a major determinant of atherosclerosis progression (25) and that increases in glycemic variation causes oxidative stress which further promotes diabetes complications (52). Recent review of studies in this area concluded that: "there are now comprehensive and consistent data from pathophysiological as well as epidemiologic studies that excessive post-load glucose excursions have acute and chronic harmful effects on the endothelium and vessel wall," (34). At the behavioral level, clinical experience suggests a relationship between postprandial hyperglycemia and acute and transient increases in psychological symptoms and cognitive disruptions. Extreme swings in BG are associated with depressive symptoms, low energy and, in the long term, with a high incidence of depression (11,22,63,69). In turn, we know that CVD and recurrent myocardial infarction (MI) are associated with depression, sedentary life style, BG variability, and poor metabolic control.

Thus, at both research and clinical levels, we are facing a complex interplay between physiology and behavior, driven and reflected by the dynamics of BG fluctuations: risk for hypoglycemia on one side and hyperglycemia-related complications on the other. This dynamic is reflected not only, and even not primarily, by average glycemia—the major display of BG fluctuations is the variability of BG across hypoglycemic and hyperglycemic values. Thus, we can conclude that the ability of patients to tightly control their glycemic variation is a paramount task in the control of diabetes. In fact, a recent review of the subject concluded that "glucose variability, considered in combination with A1C, maybe a more reliable indicator of blood glucose control and the risk for long-term complications than mean A1C alone" (37).

Because prerequisite to control is information, it becomes essential that the best currently available sources of information enabling the control of diabetes, are equipped with algorithms for evaluation the extent of glucose variability. This understanding entails creating methods for quantifying BG variability in the field from available SMBG data, validation of these methods via large representative data collection, and appropriate visual and numbering feedback of the results to patients. As detailed below, these tasks are accomplished by this invention disclosure.

Measuring Blood Glucose Variability in Diabetes:

The traditional statistical calculation of BG variability includes computing the standard deviation (SD) of SMBG readings and/or counting of hypoglycemic (BG below 3.9 mmol/l or 70 mg/dl, or some other threshold value) and hyperglycemic readings (BG above 10 mmol/l or 180 mg/dl, or some other threshold value). In addition to these traditional measures, several other measures of variability have been introduced previously:

M-value—An old variability measure (introduced in 1965) that has two versions, without and with corrections for BG range (57);

MAGE—Mean Amplitude of Glucose Excursions introduced in 1970(59);

Liability Index (LI)—A recently reported (in 2004) Index intended for assessment of severity of hypoglycemia and glycemic liability in T1DM (55).

A major problem common for these measures (except for LI) is their insensitivity to hypoglycemia and their inherent bias towards hyperglycemic readings, which is reflected by the historically poor prediction of hypoglycemic episodes (8 to 18% as reviewed in the previous section). In previous studies we have found that the basis for that poor prediction appeared to be mathematical, rather than clinical: it lies in the fact that the BG measurement scale is substantially asymmetric and skewed towards hyperglycemia (40). In other words, the "numerical center" of the data is substantially separated from its "clinical center." Thus, clinical conclusions, based on numerical methods, will be less accurate for the constricted hypoglycemic range and will be biased towards hyperglycemia. Thus, as expected and as reported in the next section, the SD of BG, the M-values and MAGE are mostly correlated to hyperglycemic episodes. The LI is very similar to our previously reported absolute BG rate of change (41)—the difference is the squared denominator in the formula. Because it is a differential statistic, it puts more emphasize on hypoglycemia than traditional BG-based statistics. Thus, as expected and as shown in the next section, the LI correlates better than SD of BG, M-value and MAGE with future significant hypoglycemic episodes. However, it is still substantially less accurate that our risk-based methods (introduced in this disclosure) in prediction of hypoglycemic episodes.

In order to correct the numerical problem created by the asymmetry of the BG scale we have introduced a mathematical transformation that symmetrizes the BG scale (40) and, based on this transformation, we developed our theory of risk analysis of BG data (47). Because this theory and the risk space that it defines serve as essential background for this invention disclosure, we will review briefly its basics:

Symmetrization of the BG Scale. The whole range of most BG reference meters is 1.1 to 33.3 mmol/L (20 to 600 mg/dl), which is considered to cover practically all observed values. The target BG range for a person with T1DM is considered to be 3.9-10 mmol/L (70-180 mg/dl). Hypoglycemia is usually identified as a BG below 3.9 mmol/L, hyperglycemia is a BG above 10 mmol/L. It is evident that this scale is not symmetric—the hyperglycemic range (10 to 33.3 mmol/L) is much greater than the hypoglycemic range (1.1-3.9 mmol/L), and the euglycemic range (3.9-10 mmol/L) is not centered within the scale. As a result, the numerical center of the scale (17.2 mmol/L) is quite distant from its "clinical center"—the clinically desired clustering of BG values of patients with diabetes of about 6-6.5 mmol/L. FIG. 1 presents the effect of this asymmetry by way of a typical BG data distribution of 186 readings downloaded from a memory meter. The distribution is substantially skewed and the superimposed normal density poorly describes the data. In order to correct this problem, we introduce a BG scale transformation, based on two clinical assumptions: A1) the whole transformed BG range is symmetric about 0; A2) the target transformed BG range is symmetric about 0. These assumptions lead to a system of nonlinear equations that yielded the transformation bringing the clinical and the numerical center of the BG scale together. As a result, the distribution of BG readings of subjects with T1DM became symmetric, i.e., statistically "normalized" (FIG. 2).

The BG Risk Space. FIG. 3 presents a quadratic risk function superimposed over the transformed BG scale. This is the BG Risk Function assigning a risk value to each BG level from 1.1 to 33.3 mmol/L (20-600 mg/dl). The "weights" of the hypo- and hyperglycemic ranges of the BG scale are balanced, ensuring that statistical procedures analyzing symmetrized and weighted SMBG data would be equally sensitive to hypoglycemic and to hyperglycemic readings. Thus, via the sequential application of the symmetrization function and the BG risk function, the standard BG measurement scale is converted into risk scale, or risk space in mathematical terms.

The Low BG Index (LBGI) is based on the left branch of the BG Risk Function and accounts for the frequency and extent of hypoglycemia (FIG. 3). The LBGI has been validated by multiple studies as an excellent predictor of future significant hypoglycemia (39,41,42,45,47). The LBGI also provides means for classification of the subjects with regard to their long-term risk for hypoglycemia into Minimal, Low, Moderate and High-risk groups, with LBGI of below 1.1, 1.1-2.5, 2.5-5.0, and above 5.0 respectively (45). The LBGI is independent from hyperglycemic episodes.

The High BG Index (HBGI) is based on the right branch of the BG Risk Function (FIG. 3) and accounts for the trends towards hyperglycemia observed in patients' SMBG records. The HBGI has been validated by multiple studies as a measure of future significant hypoglycemia (45,48). The HBGI provides means for classification of the subjects with regard to their long-term risk for hyperglycemia into: Minimal, Low, Moderate and High-risk groups, with HBGI of below 5.0, 5.0-10, 10-15, and above 15 respectively (45). The HBGI is independent from hypoglycemia. In combination, the LBGI and the HBGI cover the two extreme ends of the BG scale and provide a comprehensive risk assessment of glucose excursion.

Conclusions: The variability computations carried in risk space (risk scale) will have the following important numerical properties and clinical advantages over traditional and literature-reported measures:

Similar emphasis will be placed on the hypoglycemic and hyperglycemic ranges;

The normal BG range (3.9-10 mmol/L or 70-180 mg/dl) will be given less weight, thus variability contained within the normal range will be less important that excursions outside of this range. This corresponds to the clinical importance of extreme BG fluctuation and to the clinical understanding that fluctuations within the normal range are generally harmless;

Excursions into extreme hypoglycemia and hyperglycemia will get progressively increasing risk values, which corresponds to the clinical impression that more extreme hypoglycemia or hyperglycemia carries higher risk for the patient. This particular point contrasts the BG risk space to the traditional simple counting of hypoglycemic or hyperglycemic episodes that does not take into account the extent of these conditions.

An aspect of various embodiments of the present invention provides, but not limited thereto, a new measure of BG variability that utilizes in a novel way the risk-space representation of the BG scale providing a single numerical estimate of BG variability that is equally sensitive to hypoglycemia and hyperglycemia.

BRIEF SUMMARY OF INVENTION

The various embodiments of the present invention comprise, among other things, a new system, computer program product, method and algorithm for evaluation of blood glucose variability—one of the most important parameters of diabetes management. An embodiment of the method uses routine self-monitoring blood glucose (SMBG) data collected over a period of 2-6 weeks and is based on our previously developed theory of risk analysis of blood glucose data. For the purposes of this document, SMBG is defined as episodic non-automated determination (typically 3-5 times per day) of blood glucose at diabetic patients' natural environment. A user, subject or patient may monitor oneself or rely on the assistance of others, e.g. a lay person, acquaintance, clinician, other medical professional, etc.

Various embodiments of the present invention may pertain directly to, among other things, the following:

Enhancement of existing SMBG devices by introducing an intelligent data interpretation component capable of evaluating the extent, and predicting the risk of extreme BG fluctuations and enabling of future SMBG devices by the same features;

a Enhancement by the same features of hand-held devices (personal digital assistants, PDA) intended to assist diabetes management;

Enhancement by the same features of software that retrieves SMBG data—such software is produced by virtually every manufacturer of home BG monitoring devices and is customarily used by patients and health care providers for interpretation of SMBG data. The software can reside on patients' personal computers, or be used via Internet portal;

Evaluation of the effectiveness of various treatments for diabetes (insulin, variability lowering medications, such as pramlintide and exenatide).

Evaluation of the effectiveness of new insulin delivery devices (insulin pumps), or of future closed-loop diabetes control systems.

One aspect of an embodiment of the invention includes a method, system and computer program product for computing the Average Daily Risk Range (ADRR)—a measure of overall glucose variability. This method uses SMBG readings from a predetermined period, for example 2-6 weeks, and predicts the risk for extreme hypoglycemic and hyperglycemic excursions over the next 1-3 months. In one embodiment, the invention provides a computerized method and system using the ADRR of a patient based on SMBG data collected over a predetermined duration to evaluate glycemic variability and risk for extreme glucose excursions. In another embodiment, the invention provides a computerized method and system using the Average Daily Blood Glucose Range (BGRANGE) of a patient based on SMBG data collected over a predetermined duration to evaluate glycemic variability and risk for extreme glucose excursions.

Another aspect of the invention includes a method, system, and computer program product for estimating separately the glucose variability in the hypoglycemic range via a Low BG Index (LBGI) and the glucose variability in the high BG range via High BG Index (HBGI), followed by a combination of the two indices into a single variability display. This method uses SMBG readings from a predetermined period, for example 2-6 weeks, and predicts separately the risk for future significant hypoglycemia and the risk for future significant hyperglycemia over the next 1-3 months. In one embodiment, the invention provides a computerized method and system using the LBGI and the HBGI to evaluate the long-term risks for hypoglycemia and hyperglycemia of a patient based on SMBG data collected over a predetermined duration.

These aspects of the invention can be integrated together to provide sequential increasingly detailed levels of information about the glycemic control and the glucose variability of an individual with diabetes: the first level would be an overall variability estimate based on the ADDR, the second level would include separate presentation of risks for hypoglycemia and hyperglycemia utilizing the LBGI and the HBGI respectively.

An aspect of an embodiment of the present invention provides a method for measuring blood glucose variability. The method may comprise: acquiring a plurality of blood glucose data points; transforming the plurality of blood glucose data points according to a transforming function; calculating at least one risk value for at least some of each of the transformed plurality of blood glucose data points; calculating at least one risk range based on at least two of the calculated risk values within a period of time with a predetermined duration; and calculating at least one composite risk range based on at least one of the calculated risk ranges.

An aspect of an embodiment of the present invention provides a system for determining blood glucose variability, wherein the system comprises an acquisition module acquiring a plurality of blood glucose data points and a processor. The processor may be programmed to: transform the plurality of blood glucose data points from a blood glucose range to a transformed range according to a transforming function, calculate at least one risk value for at least some of each of the transformed plurality of blood glucose data points, calculate at least one risk range based on at least two of the calculated risk values within a period of time with a predetermined duration, and calculate at least one composite risk range based on at least one of the calculated risk ranges.

An aspect of an embodiment of the present invention provides a computer program product comprising a computer useable medium having computer program logic for enabling at least one processor in a computer system to measure blood glucose variability. The computer program logic may comprise: acquiring a plurality of blood glucose data points; transforming the plurality of blood glucose data points from a blood glucose range to a transformed range according to a transforming function; calculating at least one risk value for at least some of each of the transformed plurality of blood glucose data points; calculating at least one risk range based on at least two of the calculated risk values within a period of time with a predetermined duration; and calculating at least composite one risk range based on at least one of the calculated risk ranges.

An aspect of an embodiment of the present invention provides a method for measuring blood glucose variability. The method may comprise: 1) acquiring a plurality of self-monitored blood glucose data points, wherein the plurality of self-monitored blood glucose data points span a period of at least one day; 2) transforming the plurality of self-monitored blood glucose data points according to a transforming function, wherein the transforming function is $f(BG, \alpha, \beta, \gamma) = \gamma \cdot [(\ln(BG))^{\alpha} - \beta]$, where BG is a blood glucose value, $(\alpha, \beta, \gamma) = (1.026, 1.861, 1.794)$ if BG is measured in mM, and $(\alpha, \beta, \gamma) = (1.084, 5.381, 1.509)$ if BG is measured in mg/dl; 3) defining a BG risk space, wherein the BG risk space is $r(BG) = 10 \cdot f(BG)^2$; 4) defining a left branch of the BG risk space representing a risk of hypoglycemia as $rl(BG) = r(BG)$ if $f(BG) < 0$ and 0 otherwise; 5) defining a right branch of the BG risk space representing a risk of hyperglycemia as $rh(BG) = r(BG)$ if $f(BG) > 0$ and 0 otherwise; 6) calculating a maximal hypoglycemic risk value for the plurality of self-monitored blood glucose data points for each day as: $LR^i = \max(rl(x_1^i), rl(x_2^i), \ldots, rl(x_{n_i}^i))$, where $n_i$ is the number of readings for each day i and $x_1^i, x_2^i, \ldots, x_{n_i}^i$ are the $n_i$ self-monitored blood glucose data points for each day i; 7) calculating a maximal hyperglycemic risk value for the plurality of self-monitored blood glucose data points for each day as $HR^i = \max(rh(x_1^i), rh(x_2^i), \ldots, rh(x_{n_i}^i))$, where $n_i$ is the number of readings for each day i and $x_1^i, x_2^i, \ldots, x_{n_i}^i$ are the $n_i$ self-monitored blood glucose data points for each day i; 8) calculating an average daily risk range as $$ADRR = \frac{1}{M} \sum_{i=1}^{M} [LR^i + HR^i],$$

where the plurality of self-monitored blood glucose data points are collected on days i=1, 2, ..., M; 9) classifying the average daily risk range into one of at least four categories, wherein the at least four categories includes "Low", "Low-Moderate", "Moderate-High", and "High, wherein the "Low Risk" category corresponds to a risk range between about 0 and about 20, the "Low-Moderate Risk" category corresponds to a risk range between about 20 and about 30, the "Moderate-High Risk" category corresponds to a risk range between about 30 and about 40, and the "High Risk" category corresponds to a risk range greater than about 40; and 10) displaying the average daily risk range and the one of the at least four categories into which the average daily risk range is classified.

An aspect of an embodiment of the present invention provides a system for measuring blood glucose variability, wherein the system may comprises an acquisition module acquiring a plurality of self-monitored blood glucose data points, and wherein the plurality of self-monitored blood glucose data points span a period of at least one day. The system comprises a processor that may be programmed to: 1) transform the plurality of self-monitored blood glucose data points from a blood glucose range to a transformed range according to a transforming function, wherein the minimal and maximal values of the transformed range are $-\sqrt{10}$ and $\sqrt{10}$, respectively, wherein the transforming function is $f(BG, \alpha, \beta, \gamma) = \gamma \cdot [(\ln(BG))^{\alpha} - \beta]$, where BG is a blood glucose value, $(\alpha, \beta, \gamma) = (1.026, 1.861, 1.794)$ if BG is measured in mM, and $(\alpha, \beta, \gamma) = (1.084, 5.381, 1.509)$ if BG is measured in mg/dl; 2) define a BG risk space, wherein the BG risk space is $r(BG) = 10 \cdot f(BG)^2$; 3) define a left branch of the BG risk space representing a risk of hypoglycemia as $rl(BG) = r(BG)$ if $f(BG) < 0$ and 0 otherwise; 4) define a right branch of the BG risk space representing a risk of hyperglycemia as $rh(BG) = r(BG)$ if $f(BG) > 0$ and 0 otherwise; 5) calculate a maximal hypoglycemic risk value for the plurality of self-monitored blood glucose data points for each day as $LR^i = \max(rl(x_1^i), rl(x_2^i), \ldots, rl(x_{n_i}^i))$, where $n_i$ is the number of readings for each day i and $x_1^i, x_2^i, \ldots, x_{n_i}^i$ are the $n_i$ self-monitored blood glucose data points for each day i; 6) calculate a maximal hyperglycemic risk value for the plurality of self-monitored blood glucose data points for each day as $$HR^i = \max(rh(x_1^i), rh(x_2^i), \ldots, rh(x_{n_i}^i)),$$

where $n_i$ is the number of readings for each day i and $x_1^i, x_2^i, \ldots, x_{n_i}^i$ are the $n_i$ self-monitored blood glucose data points for each day i; and 7) calculate an average daily risk range as $$ADRR = \frac{1}{M} \sum_{i=1}^{M} [LR^i + HR^i],$$

where the plurality of self-monitored blood glucose data points are collected on days i=1, 2, ..., M; classifying the average daily risk range into one of at least four categories, wherein the at least four categories includes "Low", "Low-Moderate", "Moderate-High", and "High, wherein the "Low Risk" category corresponds to a risk range between about 0 and about 20, the "Low-Moderate Risk" category corresponds to a risk range between about 20 and about 30, the "Moderate-High Risk" category corresponds to a risk range between about 30 and about 40, and the "High Risk" category corresponds to a risk range greater than about 40; and 8) a display module displaying the average daily risk range and the one of the at least four categories into which the average daily risk range is classified.

An aspect of an embodiment of the present invention provides a computer program product comprising a computer useable medium having computer program logic for enabling at least one processor in a computer system to measure blood glucose variability. The computer program logic may comprise: 1) acquiring a plurality of self-monitored blood glucose data points, wherein the plurality of self-monitored blood glucose data points span a period of at least one day; 2) transforming the plurality of self-monitored blood glucose data points from a blood glucose range to a transformed range according to a transforming function, wherein the minimal and maximal values of the transformed range are $-\sqrt{10}$ and $\sqrt{10}$, respectively, wherein the transforming function is $f(BG, \alpha, \beta, \gamma) = \gamma \cdot [(\ln(BG))^\alpha - \beta]$, where BG is a blood glucose value, $(\alpha, \beta, \gamma) = (1.026, 1.861, 1.794)$ if BG is measured in mM, and $(\alpha, \beta, \gamma) = (1.084, 5.381, 1.509)$ if BG is measured in mg/dl; 3) defining a BG risk space, wherein the BG risk space is: $r(BG) = 10 \cdot f(BG)^2$; 4) defining a left branch of the BG risk space representing a risk of hypoglycemia as $rl(BG) = r(BG)$ if $f(BG) < 0$ and 0 otherwise; 5) defining a right branch of the BG risk space representing a risk of hyperglycemia as $rh(BG) = r(BG)$ if $f(BG) > 0$ and 0 otherwise; 6) calculating a maximal hypoglycemic risk value for the plurality of self-monitored blood glucose data points for each day as $LR^i = \max(rl(x_1^i), rl(x_2^i), \ldots, rl(x_{n_i}^i))$, where $n_i$ is the number of readings for each day i and $x_1^i, x_2^i, \ldots, x_{n_i}^i$ are the $n_i$ self-monitored blood glucose data points for each day i; 7) calculating a maximal hyperglycemic risk value for the plurality of self-monitored blood glucose data points for each day as $HR^i = \max(rh(x_1^i), rh(x_2^i), \ldots, rh(x_{n_i}^i))$, where $n_i$ is the number of readings for each day i and $x_1^i, x_2^i, \ldots, x_{n_i}^i$ are the $n_i$ self-monitored blood glucose data points for each day i; 8) calculating an average daily risk range as $$ADRR = \frac{1}{M} \sum_{i=1}^{M} [LR^i + HR^i],$$

where the plurality of self-monitored blood glucose data points are collected on days $i = 1, 2, \ldots, M$; 9) classifying the average daily risk range into one of at least four categories, wherein the at least four categories includes "Low", "Low-Moderate", "Moderate-High", and "High, wherein the "Low Risk" category corresponds to a risk range between about 0 and about 20, the "Low-Moderate Risk" category corresponds to a risk range between about 20 and about 30, the "Moderate-High Risk" category corresponds to a risk range between about 30 and about 40, and the "High Risk" category corresponds to a risk range greater than about 40; and 10) displaying the average daily risk range and the one of the at least four categories into which the average daily risk range is classified.

An aspect of an embodiment of the present invention provides a method for measuring blood glucose variability. The method may comprise: acquiring a plurality of blood glucose data points; calculating at least one risk range based on at least two of the plurality of blood glucose data points within a period of time with a predetermined duration; and calculating at least one average predetermined duration blood glucose risk range based on at least one of the calculated risk ranges.

An aspect of an embodiment of the present invention provides a system for measuring blood glucose variability, wherein the system may comprises an acquisition module acquiring a plurality of blood glucose data points and a processor. The processor may be programmed to: calculate at least one risk range based on at least two of the plurality of blood glucose data points within a period of time with a predetermined duration, and calculate at least one average predetermined duration blood glucose risk range based on at least one of the calculated risk ranges.

An aspect of an embodiment of the present invention provides a computer program product comprising a computer useable medium having computer program logic for enabling at least one processor in a computer system to measure blood glucose variability. The computer program logic may comprise: acquiring a plurality of blood glucose data points; calculating at least one risk range based on at least two of the plurality of blood glucose data points; and calculating at least one average daily blood glucose risk range based on at least one of the calculated daily risk ranges.

These and other advantages and features of the invention disclosed herein, will be made more apparent from the description, drawings and claims that follow.

BRIEF SUMMARY OF THE DRAWINGS

In order to facilitate a fuller understanding of the present invention, reference is now made to the appended drawings. These drawings should not be construed as limiting the present invention, but are intended to be exemplary only.

DETAILED DESCRIPTION OF THE INVENTION

Figure 1:
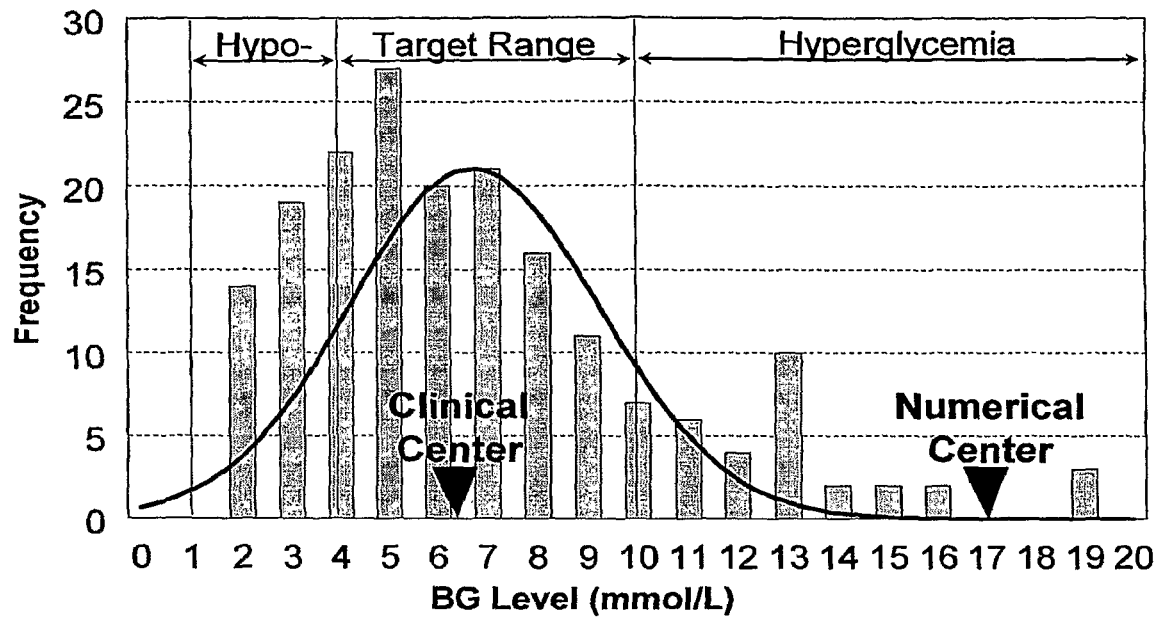
FIG. 1: Graphical representation of typical distribution of SMBG readings of a person with diabetes.
Figure 2:
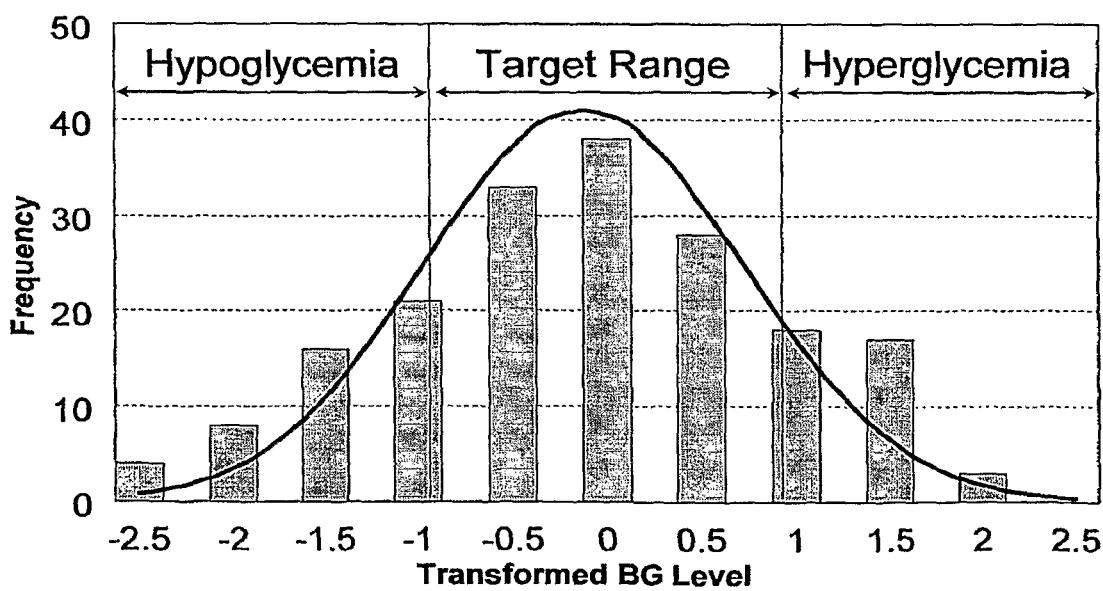
FIG. 2: Graphical representation of the distribution of the transformed BG readings from FIG. 1.

The various embodiments of the present invention uses, among other things, the theoretical background established by our theory of risk analysis of BG data (40,41,47) and follows previously developed and disclosed technology (49, 50). We present first the theoretical/mathematical base of this invention. All formulas are included together with software code for computation of the key component of the subsequent algorithms. Then we present the algorithm for computation of the ADRR. The algorithms computing the LBGI and HBGI have been disclosed previously (49,50). Finally, the results of the algorithms are combined in a structured display.

Theoretical Mathematical Base:

The BG levels are measured in mg/dl in the USA and in mmol/L (or mM) most elsewhere. The two scales are directly related by 18 mg/dl=1 mM. The whole range of most BG reference meters is 1.1 to 33.3 mM, which is considered to cover practically all observed values. The target BG range for a person with diabetes is considered to be 3.9 to 10 mM. Hypoglycemia is identified as a BG below 3.9 mM, hyperglycemia is a BG above 10 mM. This scale is numerically asymmetric—the hyperglycemic range (10 to 33.3 mM) is greater that the hypoglycemic range (1.1-3.9 mM) and the euglycemic range (3.9-10 mM) is not centered within the scale. We correct this asymmetry by introducing a transformation f(BG)—a continuous function defined on the BG range [1.1, 33.3] that has the general two-parameter analytical form:

$$f(BG, \alpha, \beta) = [(\ln(BG))^\alpha - \beta], \alpha, \beta > 0$$

and satisfies the assumptions:

A1: $f(33.3, \alpha, \beta) = -f(1.1, \alpha, \beta)$ and
A2: $f(10, \alpha, \beta) = -f(3.9, \alpha, \beta)$.

By multiplying by a third parameter γ we fix the minimal and maximal values of the transformed BG range at $-\sqrt{10}$ and $\sqrt{10}$ respectively. These values are convenient for two reasons: first, a random variable with a central normal distribution would have 99.8% of its values within the interval $[-\sqrt{10}, \sqrt{10}]$, and second, this provides a calibration of the BG risk function from 0 to 100 (see the next section). This scaling and the assumptions A1 and A2 lead to the equations:

$$(\ln(33.3))^\alpha - \beta = -[(\ln(1.1))^\alpha - \beta]$$

$$(\ln(10.0))^\alpha - \beta = -[(\ln(3.9))^\alpha - \beta]$$

$$\gamma \cdot [(\ln(33.3))^\alpha - \beta] = -\gamma \cdot [(\ln(1.1))^\alpha - \beta] = \sqrt{10}$$

which are easily reduced to a single nonlinear equation for the parameter α. When solved numerically under the restriction α>0, it gives: α=1.026, β=1.861 and γ=1.794. If BG is measured in mg/dl, we obtain α=1.084, β=5.381, γ=1.509.

Thus, when BG is measured in mM, $f(BG) = 1.794 \cdot [(\ln(BG))^{1.026} - 1.861]$. The whole BG range is transformed into the symmetric interval $[-\sqrt{10}, \sqrt{10}]$. The target BG range is transformed into the symmetric interval [-0.9, 0.9]. Since f(6.25)=0, the transformation sets the center of the transformed scale at BG=6.25 mM.

Figure 3:
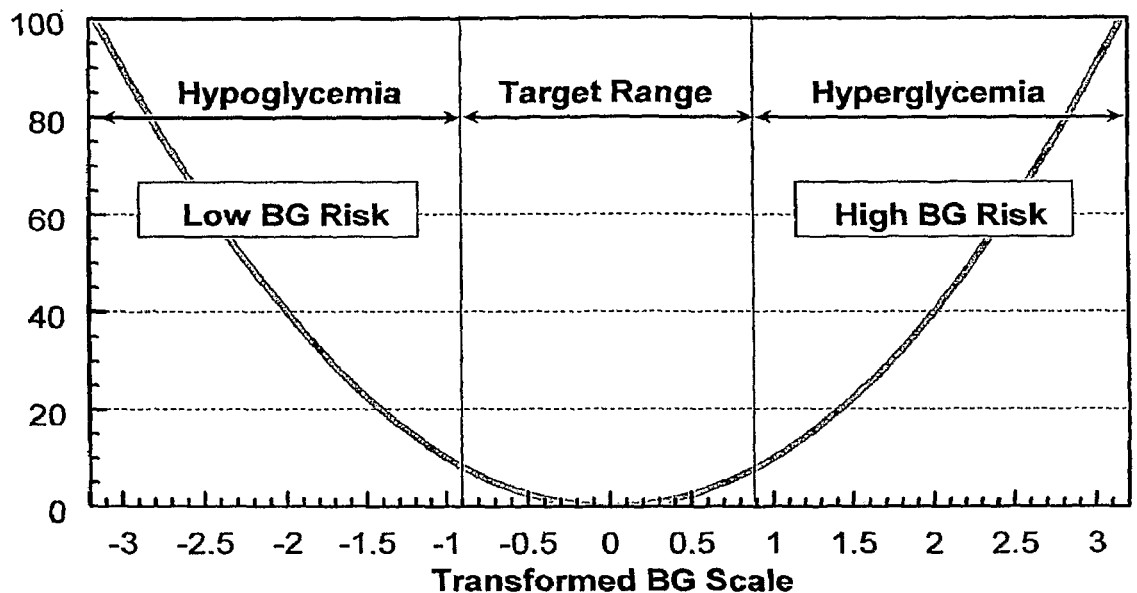
FIG. 3: Graphical representation of the BG risk function—the base for defining the BG risk scale (risk space)

After fixing the parameters of f(BG) depending on the measurement scale that is being used, we define the quadratic function $r(BG) = 10 \cdot f(BG)^2$ (FIG. 3), which defines the BG Risk Space. The function r(BG) ranges from 0 to 100. Its minimum value is 0 and is achieved at BG=6.25 mM, a safe euglycemic BG reading, while its maximum is reached at the extreme ends of the BG scale 1.1 mM and 33.3 mM.

Thus, r(BG) can be interpreted as a measure of the risk associated with a certain BG level. The left branch of this parabola identifies the risk of hypoglycemia, while the right branch identifies the risk of hyperglycemia. These branches are identified by the formulas:

$rl(BG) = r(BG)$ if $f(BG) < 0$ and 0 otherwise (left branch);

$rh(BG) = r(BG)$ if $f(BG) > 0$ and 0 otherwise (right branch).

One of ordinary skill in the art should appreciate that other transformation functions f(BG) may be used. Similarly, other risk functions r(BG) may be used. These functions may be varied as required or desired to practice the various embodiments of the invention.

2. Defining the Average Daily Risk Range (ADRR):

Let $x_1^1, x_2^1, \ldots, x_{n_1}^1$ be a series of $n_1$ SMBG readings taken on Day 1;

Let $x_1^2, x_2^2, \ldots, x_{n_2}^2$ be a series of $n_2$ SMBG readings taken on Day 2;

. . .

Let $x_1^M, x_2^M, \ldots, x_{n_M}^M$ be a series of $n_M$ SMBG readings taken on Day M.

Where $n_1, n_2, \ldots, n_M$ are each preferably greater than or equal to 3. The number of days of observation M may be from about 7 to about 14 (about 1-2 weeks) or over about 42 (6 weeks), but is preferably between about 14 and about 42 (around 2 to 6 weeks), specifically about 28 (about 4 weeks). The total number of observations may be from about 30-75 or greater than about 75, but is preferably about 75 blood glucose data points.

The series of $n_i$ readings may be taken for periods of time with a predetermined duration outside of a day, i.e. a twenty-four hour period. For instance, the first series of readings may be taken over the course of about a daytime (e.g., morning and/or afternoon), then the next series taken over the course of about a nighttime (e.g., afternoon and/or night), and so forth, such that each period of time with a predetermined duration may be about a daytime or about a nighttime in a daytime/nighttime cycle. In some instances, each series of readings may be taken over predetermined durations less than about a twenty-four hour period. In another instance, each series of readings may be taken over the course of less than a week. In another instance, each series of readings may be taken over the course of about a week. In yet other instances, each series of readings may be taken over predetermined durations greater than about a daytime or about a nighttime in a daytime/nighttime cycle but less than about a twenty-four hour period. In another instance, the predetermined duration may be greater than a twenty-four hour period, but less than about a week. In another instance, the predetermined duration may be greater than a week or plurality of weeks.

It should be appreciated that the number and/or periods of observations may vary as required or desired to practice the various aspects of the invention. It should be appreciated that any or all of the periods may vary in duration as desired or required.

Further, let $$LR^i = \max(rl(x_1^i), rl(x_2^i), \ldots, rl(x_{n_i}^i)) \text{ and}$$

$HR^i = \max(rh(x_1^i), rh(x_2^i), \ldots, rh(x_{n_i}^i))$ for day #i;
i=1,2, ... M.

The Average Daily Risk Range and the Average Daily BG Range are then defined as:

$$ADRR = \frac{1}{M} \sum_{i=1}^{M} [LR^i + HR^i]$$

$$BGRANGE = \frac{1}{M} \sum_{i=1}^{M} \left[ \max_{j=1,n_i}(x_j^i) - \min_{j=1,n_i}(x_j^i) \right]$$

3. Possible Variations of the ADRR:

Various perturbations of the formulas computing the ADRR are possible that would lead to similar results in estimation of glucose variability. For example, the BG risk function and the BG risk space can be defined on the basis of absolute value, not square, which would change the formula to r(BG)=10·abs[f(BG)], placing less weight on extreme BG excursions. In general the possible variations of the ADRR can be classified as follows:

3.1. Different Weightings: The weight on BG extremes can be controlled by introducing and varying a "weighing" parameter was follows: $r(BG; w)=10 \cdot |f(BG)|^w$, where the weight w>0. In the case of the quadratic risk function described above, the weighting parameter is set to w=2. A larger weighting parameter would place more weight on extreme BG fluctuations.

3.2. Different Summation Formulas: Another version of the ADRR can be computed by using the standard deviation of the daily risk ranges instead of their average. In this case, the formula will be modified as follows:

$$SDRR^2 = \frac{1}{M-1} \sum_{i=1}^{M} [(LR^i + HR^i) - \text{mean}(LR^i + HR^i)]^2$$

In our test trials, the ADRR and the SDRR resulted in similar (with a slight advantage to ADRR) evaluation of BG variability.

3.3. Different BG Scales: Finally, average daily blood glucose range, or its standard deviation, can be computed without initial transformation of the SMBG readings into risk space. In this case, these measures will be heavily influenced by high SMBG readings and will be less (or not at all) sensitive to hypoglycemia. The use of such non-symmetrized measures, (such as BGRANGE or its standard deviation) is justified only in cases where the main interest falls on postprandial glycemic excursions into the hyperglycemic range.

Alternatively, the BG scale can be transformed using any logarithmic-type transformation that similarly to f(BG) will result in approximately symmetric distribution of typical sets of SMBG readings. Out of these numerous possibilities, the f(BG) as defined above is distinguished by its relevance to the current understanding of target BG range. If this understanding evolves in the future to another, perhaps narrower, target range, the mathematical definition of f(BG) will change accordingly.

4. Software Code for Computing the ADRR and BGRANGE:

4.1. The first step is to transform each SMBG reading into risk space. The code below assumes that the SMBG readings are stored in mg/dl:

```
SCALE=(ln(BGMG))**1.08405 - 5.381
RISK=22.765*SCALE2*SCALE
RL=0
IF (BGMG le 112.5) RL=RISK
RH=0
IF (BGMG gt 112.5) RH=RISK
```

If the readings are stored in mmol/l the parameters of the transformation should be replaced as described in the previous section:

```
SCALE=(ln(BGMM))**1.026 - 1.861
RISK=32.185*SCALE*SCALE
RL=0
IF (BGMM le 6.25) RL=RISK
RH=0
IF (BGMM gt 6.25) RH=RISK
```

4.2. The second step of the code is to compute the risk and the BG range of the N(I) readings for each day I:

```
LR(I) = max (RL(1), RL(2), ... . RL(N(I)))
HR(I) = max (RH(1), RH(2), ... . RH(N(I)))
MAXBG(I) = max (BGMG(1), BGMG(2), ... . BGMG(N(I)))
MINBG(I) = min (BGMG(1), BGMG(2), ... . BGMG(N(I)))
```

4.3. The third step of the code includes computing the ADRR as the average of daily risk ranges for days I=1, 2, . . . , M of SMBG observation:

```
ADRR = mean{[LR(1)+HR(1)],[LR(2)+HR(2)],....,[LR(M)+HR(M)]}
BGRANGE = mean{[MAXBG(1)-MINBG(1)],....,[MAXBG(M)-MINBG(M)]}
```

The LBGI and the HBGI are computed as previously described (49,50).

4.4. Finally, the ADRR may be classified in one of four categories: Low, Low-Moderate, Moderate-High, and High Risk defined by the cutoff points of ADRR<20, 20-30, 30-40, and >ADRR>40. Similarly, the LBGI and the HBGI are each classified in one of four categories: Low, Low-Moderate, Moderate-High, and High Risk for hypoglycemia and hyperglycemia respectively, defined by the cutoff points of LBGI<1.1, 1.1-2.5, 2.5-5 and >5, and the cutoff points of HBGI<5, 5-10, 10-15, and >15.

This classification may be used only for display purposes and the cutoff points for each of the three measures can be changed in various embodiments of the invention; or the measures can be used as continuous variables, without specifying cutoff points.

The other possible variants of the ADRR described above will require corresponding changes in the software code that are apparent to anyone skilled in the art of statistical computing.

5. Initial Development of the ADRR:

The ADRR was first developed using re-analysis of archival data for N=177 participants in previous LifeScan-sponsored studies (Phase 2), 90 of whom had Type 1 diabetes, and the rest had Type 2 diabetes. The demographic characteristics of these subjects are given in Table 1:

TABLE 1

Demographic characteristics and SMBG frequency of the participants

|  | T1DM (N = 90) | T2DM (N = 87) |
|---|---|---|
| Average (SD) age in years | 40.7 (11.2) | 50.2 (8.0) |
| Gender: % Male | 43% | 39% |
| Body mass index | 25.3 (4.4) | 36.3 (9.2) |
| Duration of diabetes (years) | 20.0 (10.7) | 12.2 (8.5) |
| Baseline HbA$_{1c}$ | 7.6 (1.2) | 8.8 (2.0) |
| Average number of SMBG readings per day during the study | 5.4 (2.3) | 3.5 (0.8) |

The criterion for efficiency of a variability measure was its accuracy in predicting future extreme glycemic events. In order to test potential variability measures we did the following analyses:

In this study, the participants performed SMBG for 4 months. Several variability measures were computed from the first month of routine SMBG and then were correlated with the number of extreme hypoglycemic and hyperglycemic events recorded in the following three months of investigation. The measures tested during this initial development were:

Measures Average glycemia:

MBG=Average BG during the initial observation period (Month 1);

Standard variability measures:
SBG=Standard Deviation of BG;
CVBG=BG Coefficient of variation (=SBG/MBG);
Counts of events:
N70=#episodes below 70 during month 1;
N180=#episodes above 180 during month 1;
N70-180=N70+N180;
Measures of BG dynamics (introduced by Kovatchev et al., 41):
ABSRATE=Absolute BG rate of change (for readings<4 hours apart);
Risk measures (introduced by Kovatchev et al, 41, 47):
LBGI=Low BG Index;
HBGI=High BG Index;
RISK=LBGI+HBGI;
ADRR=Average Daily Risk Range, the subject of this invention disclosure;
BGRANGE=Average BG range per day (for days with >=3 readings).

The dependent measures used for testing were therefore the number of future extreme glycemic episodes recorded in months 2-4 (days 31-120) of study in the following categories:

NSEVLOW=#significant hypoglycemic episodes; BG<=39 mg/dl;
NLOW=#hypoglycemic episodes; BG<=70 mg/dl;
NNOR=#readings within normal (70-180) range;
NHIGH=#hyperglycemic episodes; BG>180 mg/dl;
NSEVHI=#significant hyperglycemic episodes; BG>400 mg/dl.

Results: Table 2 presents the results from this initial development. Correlations and significance levels are given, which show that the ADRR is the best overall measure of glycemic variability in this data set. Separately in the hypoglycemic and hyperglycemic ranges, the best variability measures were the LBGI and the HBGI, respectively:

TABLE 2

Results from the Initial Development Based on Archival Data

|  | NSEVLOW | NLOW | NNOR | NHIGH | NSEVHI |
|---|---|---|---|---|---|
| Measures Average glycemia: | | | | | |
| MBG | −0.236 | −0.3328 | −0.4801 | 0.613 | 0.5306 |
|  | P = .002 | P = .000 | P = .000 | P = .000 | P = .000 |
| Standard variability measures: | | | | | |
| SBG | 0.1275 | 0.1648 | −0.2878 | 0.4952 | 0.5497 |
|  | P = .091 | P = .028 | P = .000 | P = .000 | P = .000 |
| CVBG | 0.4813 | 0.571 | 0.0295 | 0.1981 | 0.2214 |
|  | P = .000 | P = .000 | P = .697 | P = .008 | P = .003 |
| Counts of events: | | | | | |
| N70 | 0.7374 | 0.8848 | 0.3942 | −0.0221 | −0.0441 |
|  | P = .000 | P = .000 | P = .000 | P = .770 | P = .560 |
| N180 | −0.0355 | −0.0266 | −0.2071 | 0.8021 | 0.4678 |
|  | P = .639 | P = .725 | P = .006 | P = .000 | P = .000 |
| N70-180 | 0.4238 | 0.5222 | 0.0645 | 0.6769 | 0.3756 |
|  | P = .000 | P = .000 | P = .393 | P = .000 | P = .000 |
| Measures of BG dynamics: | | | | | |
| ABSRATE | −0.0577 | −0.0509 | −0.0685 | −0.0002 | 0.0264 |
|  | P = .447 | P = .502 | P = .367 | P = .998 | P = .728 |
| Risk measures | | | | | |
| LBGI | 0.7956 | 0.6656 | 0.1105 | −0.098 | −0.0114 |
|  | P = .000 | P = .000 | P = .143 | P = .194 | P = .880 |
| HBGI | −0.107 | −0.1893 | −0.4741 | 0.6296 | 0.604 |
|  | P = .156 | P = .012 | P = .000 | P = .000 | P = .000 |
| RISK | 0.3413 | 0.1915 | −0.3855 | 0.539 | 0.563 |
|  | P = .000 | P = .011 | P = .000 | P = .000 | P = .000 |

TABLE 2-continued

Results from the Initial Development Based on Archival Data

|  | NSEVLOW | NLOW | NNOR | NHIGH | NSEVHI |
|---|---|---|---|---|---|
| ADRR | 0.6314 | 0.5494 | −0.0781 | 0.4792 | 0.4423 |
|  | P = .000 | P = .000 | P = .301 | P = .000 | P = .000 |
| BGRANGE | 0.2499 | 0.3932 | 0.0383 | 0.6242 | 0.4803 |
|  | P = .001 | P = .000 | P = .612 | P = .000 | P = .000 |

6. Prospective Validation of ADRR:

Using a large data set independently collected at LifeScan (N=335 subjects), the ADRR and its standard deviation (SDRR) were extensively tested against all standard measures of glycemic control and glucose variability presented in the previous section, and against all known to us measures of variability reported in the literature. Table 3 presents demographic characteristics of the participants in the validation data set:

TABLE 3

Demographic characteristics and SMBG frequency in the validation data set:

| | |
|---|---|
| Age distribution: <20, 20-40, >40 years | 24.5%, 22.4%, 48.4%* |
| Gender: % Male vs. Female | 39% vs. 56.1%* |
| Race: White, African American, Hispanic, Native American, Asian, Other or missing | 76.7%, 12.8%, 4.2%, 0.6%, 0.3%, 5.4% |
| Type of diabetes: % T1DM vs. T2DM | 75.8% vs. 24.2% |
| Baseline HbA$_{1c}$ (SD) | 8.1 (1.3) |
| Average number of SMBG readings per day during the study (SD) | 4.1 (1.8) |

*For these characteristics there were missing data, which results in percentages not adding up to 100%:

The measures included in the validation analyses and tested against ADRR and SDRR were:

Measures Average Glycemia:
 HBA1C=HbA1c—"gold standard" measure of glycemic control (1,56);
 MBG=Average BG during the initial observation period (Month 1);
Standard Variability Measures:
 SBG=Standard Deviation of BG;
 CVBG=BG Coefficient of variation (=SBG/MBG);
Counts of Events:
 N70=#episodes below 70 during month 1;
 N180=#episodes above 180 during month 1;
 N70-180=N70+N180;
Literature Measures of Glycemic Variability:
 MVALUE=M-value (57);
 MAGE=Mean amplitude of glycemic excursions (59);
 LI=Liability Index (55);
Measures of BG dynamics ((introduced by Kovatchev et al, 41):
 ABSRATE=Absolute BG rate of change (for readings<4 hours apart);
Risk measures (introduced by Kovatchev et al 41, 47):
 LBGI=Low BG Index;
 HBGI=High BG Index;
 RISK=LBGI+HBGI.
 BGRANGE=Average BG range per day (for days with >=3 readings);
 SDRANGE=Standard deviation of BG range per day;
Validation Criteria: Following the clinical meaning of glucose variability, the criterion for efficiency of a measure was its accuracy in predicting future extreme glycemic events. Thus, all measures listed above were computed from the first month of routine SMBG and then were correlated with the number of extreme hypoglycemic and hyperglycemic events recorded in months 2-4 of investigation. The dependent measures used for testing were therefore the number future extreme glycemic episodes recorded in month 2 (days 31-60), months 2-3 (days 31-90) and months 2-4 (days 31-120) of study in the following categories. These three time intervals were used to assess the decline in prediction accuracy with increasing time horizon:

NSEVLOW=#significant hypoglycemic episodes; BG<=39 mg/dl;

NLOW=#hypoglycemic episodes; BG<=70 mg/dl;

NNOR=#readings within normal (70-180) range;

NHIGH=#hyperglycemic episodes; BG>180 mg/dl;

NSEVHI=#significant hyperglycemic episodes; BG>400 mg/dl.

Validation Results: Tables 4A, 4B, and 4C present correlations of variability measures computed from Month 1 data with extreme hypoglycemic and hyperglycemic events registered during month 2, months 2-3 and months 2-4 of study, respectively:

TABLE 4A

Correlations of Variability Measures with Extreme Glycemic Events in Month 2:

| Month 2: | NSEVLOW | NLOW | NNOR | NHIGH | NSEVHI |
|---|---|---|---|---|---|
| Measures Average glycemia: | | | | | |
| HBA1C | −0.1051 | −0.3221 | −0.5128 | 0.3446 | 0.5825 |
| MBG | −0.1753 | −0.3709 | −0.563 | 0.3588 | 0.6095 |
| Standard variability measures: | | | | | |
| SBG | 0.1538 | 0.1157 | −0.4239 | 0.2926 | 0.6465 |
| CVBG | 0.3757 | 0.4967 | −0.0874 | 0.0813 | 0.2609 |
| Counts of events: | | | | | |
| N70 | 0.6720 | 0.8324 | 0.3603 | −0.0218 | −0.0442 |
| N180 | 0.1005 | 0.0814 | −0.0156 | 0.6623 | 0.2994 |
| N70-180 | 0.4255 | 0.4913 | 0.1704 | 0.5392 | 0.2263 |
| Literature measures of glycemic variability: | | | | | |
| MVALUE | 0.1668 | −0.0165 | −0.5107 | 0.2923 | 0.745 |
| MAGE | 0.1658 | 0.1186 | −0.4186 | 0.2616 | 0.6416 |
| LI | 0.4397 | 0.4659 | 0.1427 | 0.396 | 0.3865 |
| Measures of BG dynamics: | | | | | |
| ABSRATE | 0.1807 | 0.0221 | −0.0682 | 0.0963 | 0.1716 |
| Risk measures | | | | | |
| LBGI | 0.6534 | 0.698 | 0.1358 | −0.1155 | 0.0081 |
| HBGI | −0.0751 | −0.2448 | −0.5626 | 0.3383 | 0.6960 |
| RISK | 0.1856 | 0.0297 | −0.5216 | 0.3001 | 0.716 |
| ADRR | 0.4918 | 0.4541 | −0.1473 | 0.3706 | 0.5577 |
| SDRR | 0.4636 | 0.379 | −0.2042 | 0.2567 | 0.4575 |
| BGRANGE | 0.3023 | 0.3695 | −0.0057 | 0.4404 | 0.4792 |
| SDRANGE | 0.1477 | 0.0986 | −0.4233 | 0.2079 | 0.5748 |

TABLE 4B

Correlations of Variability Measures with
Extreme Glycemic Events in Months 2-3:

| Months 2-3: | NSEVLOW | NLOW | NNOR | NHIGH | NSEVHI |
|---|---|---|---|---|---|
| Measures Average glycemia: | | | | | |
| HBA1C | 0.0241 | −0.1781 | −0.3423 | 0.4117 | 0.5806 |
| MBG | −0.0987 | −0.2841 | −0.4431 | 0.4228 | 0.6101 |
| Standard variability measures: | | | | | |
| SBG | 0.2245 | 0.2218 | −0.4025 | 0.2547 | 0.6147 |
| CVBG | 0.3666 | 0.5217 | −0.1888 | −0.0391 | 0.2052 |
| Counts of events: | | | | | |
| N70 | 0.5186 | 0.7134 | 0.1246 | −0.1771 | −0.0956 |
| N180 | 0.1107 | 0.1002 | −0.0572 | 0.529 | 0.2458 |
| N70-180 | 0.356 | 0.4464 | 0.0159 | 0.3492 | 0.1555 |
| Literature measures of glycemic variability: | | | | | |
| MVALUE | 0.1968 | 0.0523 | −0.4673 | 0.3099 | 0.7225 |
| MAGE | 0.2438 | 0.2253 | −0.3996 | 0.217 | 0.6012 |
| LI | 0.4406 | 0.4885 | 0.0321 | 0.2034 | 0.2921 |
| Measures of BG dynamics: | | | | | |
| ABSRATE | 0.2936 | 0.1472 | 0.024 | 0.1662 | 0.2653 |
| Risk measures | | | | | |
| LBGI | 0.5435 | 0.6527 | −0.0168 | −0.2184 | −0.0399 |
| HBGI | −0.0114 | −0.1664 | −0.4781 | 0.3822 | 0.6834 |
| RISK | 0.2049 | 0.0893 | −0.4977 | 0.3054 | 0.6859 |
| ADRR | 0.4809 | 0.4962 | −0.2238 | 0.243 | 0.4929 |
| SDRR | 0.4841 | 0.4837 | −0.2118 | 0.2079 | 0.4530 |
| BGRANGE | 0.3413 | 0.438 | −0.0675 | 0.2639 | 0.3923 |
| SDRANGE | 0.2086 | 0.1935 | −0.3954 | 0.2087 | 0.5609 |

TABLE 4C

Correlations of Variability Measures with
Extreme Glycemic Events in Months 2-4:

| Months 2-4: | NSEVLOW | NLOW | NNOR | NHIGH | NSEVHI |
|---|---|---|---|---|---|
| Measures Average glycemia: | | | | | |
| HBA1C | −0.0405 | −0.2068 | −0.319 | 0.3947 | 0.576 |
| MBG | −0.1458 | −0.293 | −0.4005 | 0.4025 | 0.5821 |
| Standard variability measures: | | | | | |
| SBG | 0.1539 | 0.1313 | −0.3757 | 0.2287 | 0.5764 |
| CVBG | 0.3339 | 0.4316 | −0.1692 | −0.0588 | 0.1772 |
| Count of events: | | | | | |
| N70 | 0.5993 | 0.7294 | 0.1875 | −0.183 | −0.1151 |
| N180 | 0.0563 | 0.038 | −0.0332 | 0.4707 | 0.2256 |
| N70-180 | 0.3519 | 0.4029 | 0.0679 | 0.2978 | 0.1288 |
| Literature measures of glycemic variability: | | | | | |
| MVALUE | 0.1649 | 0.0279 | −0.4125 | 0.284 | 0.6760 |
| MAGE | 0.1661 | 0.1298 | −0.378 | 0.1935 | 0.5623 |
| LI | 0.3681 | 0.3909 | 0.0363 | 0.169 | 0.2639 |
| Measures of BG dynamics: | | | | | |
| ABSRATE | 0.2741 | 0.1207 | 0.0255 | 0.1633 | 0.2465 |
| Risk measures | | | | | |
| LBGI | 0.5872 | 0.6333 | 0.0183 | −0.2263 | −0.0639 |
| HBGI | −0.0549 | −0.1845 | −0.4296 | 0.3589 | 0.6457 |
| RISK | 0.1777 | 0.063 | −0.4338 | 0.2784 | 0.6376 |
| ADRR | 0.4426 | 0.4246 | −0.1785 | 0.2044 | 0.4456 |
| SDRR | 0.4422 | 0.4098 | −0.1686 | 0.1955 | 0.4236 |
| BGRANGE | 0.2754 | 0.3353 | −0.0624 | 0.2211 | 0.3551 |
| SDRANGE | 0.16 | 0.1239 | −0.3616 | 0.194 | 0.5239 |

Tables 4A, 4B and 4C demonstrate that the ADRR is the best overall measure of glycemic variability, predictive of both future extreme hypoglycemic and hyperglycemic events over various time horizons. Thus, in our further analyses below we concentrate on detailed investigation of the predictive properties of the ADRR.

Table 5 presents the absolute number and the proportion of total readings of hypoglycemic (BG<70 mg/dl), euglycemic (70-180 mg/dl) and hyperglycemic (BG>180 mg/dl) events registered during Month 2 of investigation and stratified by six categories of the ADRR computed from Month 1 of investigation. Table 5 shows that the likelihood for both hypoglycemia and hyperglycemia sharply increases with increasing category of the ADRR. This association is supported by highly significant Chi-square tests (all p-values below 0.0001):

TABLE 5

Frequency of Prospective BG events
along the categories of ADRR:

| | BG Level | | |
|---|---|---|---|
| ADRR | BG < 70 events/total readings | # 70 <= BG <= 18 events/total readings | # BG > 180 events/total readings |
| ADRR < 10 | 68/2040 3.3% | 1753/2040 85.9% | 219/2040 10.7% |
| 10 <= ADRR < 20 | 277/4667 5.9% | 3278/4667 70.2% | 1112/4667 23.8% |
| 20 <= ADRR < 30 | 726/7788 9.3% | 4398/7788 56.5% | 2664/7788 34.2% |
| 30 <= ADRR < 40 | 1917/13103 14.6% | 6566/13103 50.1% | 4620/13103 35.3% |
| 40 <= ADRR < 50 | 1218/7517 16.2% | 3108/7517 41.3% | 3191/7517 42.4% |
| ADRR >= 50 | 1325/5884 22.5% | 2194/5884 37.3% | 2365/5884 40.2% |

Figure 4:
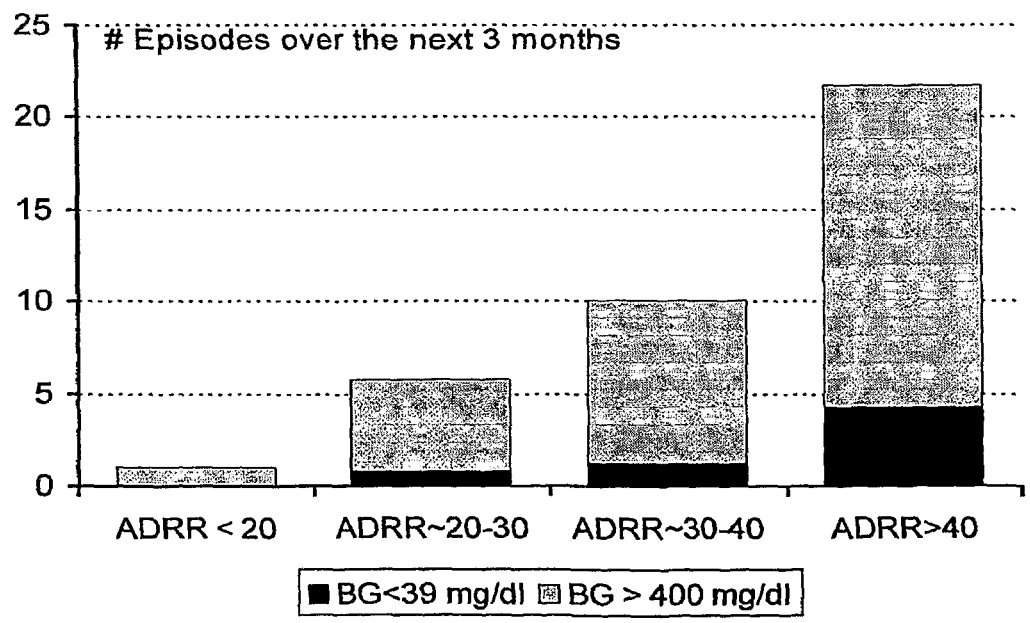
FIG. 4: Graphical representation of three months of extreme hypoglycemic and hyperglycemic episodes predicted by the categories of the ADRR.
Figure 5:
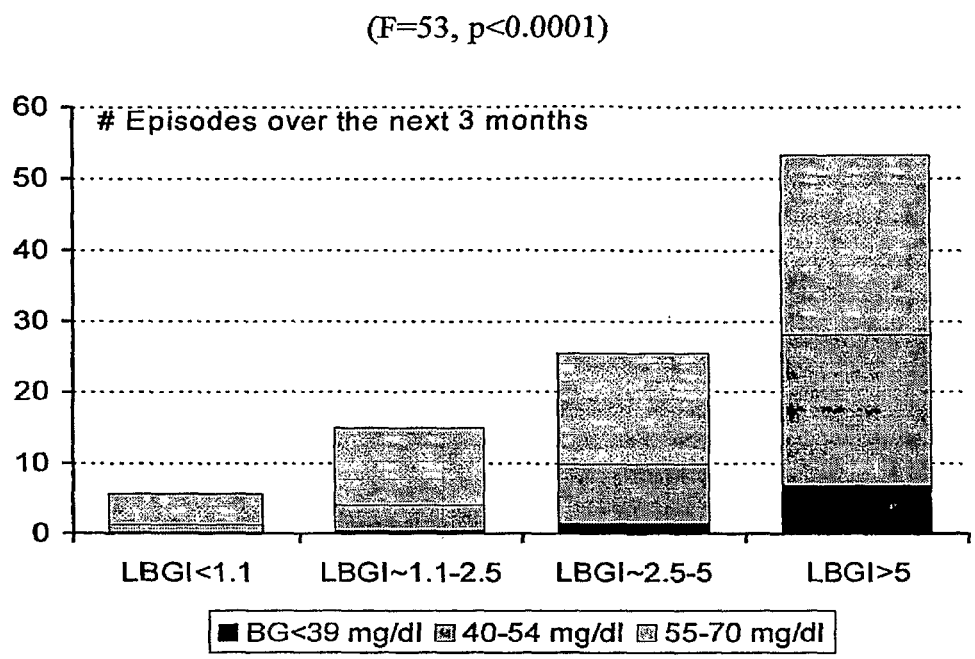
FIG. 5: Graphical representation of three months of significant hypoglycemic episodes predicted by the categories of the LBGI.
Figure 6:
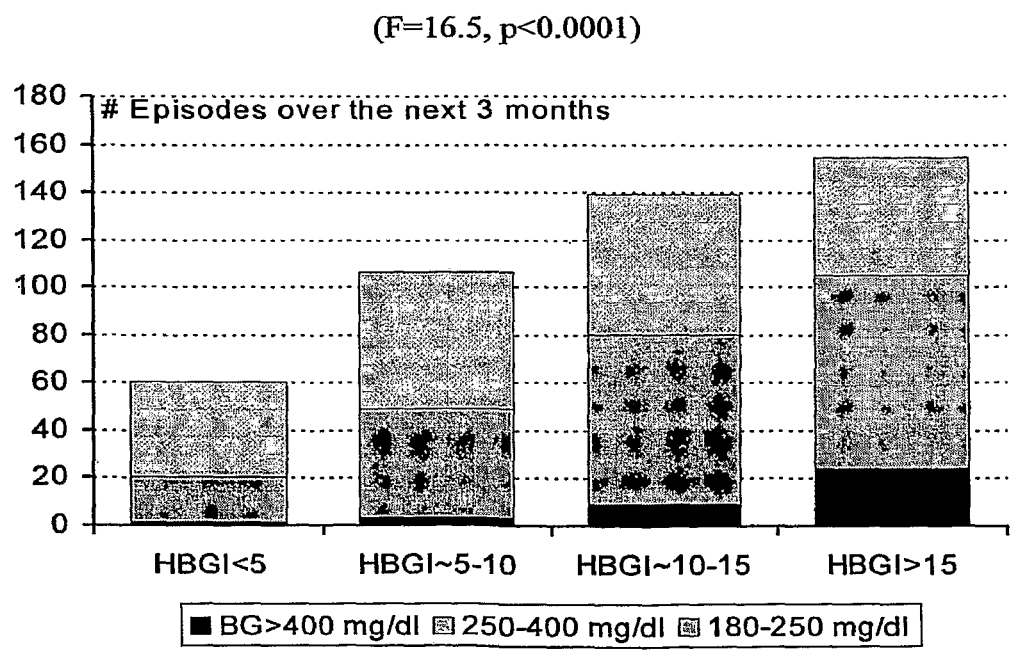
FIG. 6: Graphical representation of three months of significant hyperglycemic episodes predicted by the categories of the HBGI

Classification of ADRR: Based on this analysis and on the distribution of ADRR values across the studied populations, we suggest ADRR to be considered in the following four categories: Low Risk: ADRR<20; Low-Moderate Risk: 20<=ADRR<30; Moderate-High Risk: 30<=ADRR<40, and High Risk: ADRR>40. FIG. 4 presents the number (3 months ahead in time) of extreme hypoglycemic and hyperglycemic episodes predicted by the categories of the ADRR. FIGS. 5 and 6 present similar classification of hypoglycemic and hyperglycemic events along the categories of the LBGI and HBGI (defined in Section 3), respectively.

Figure 7:
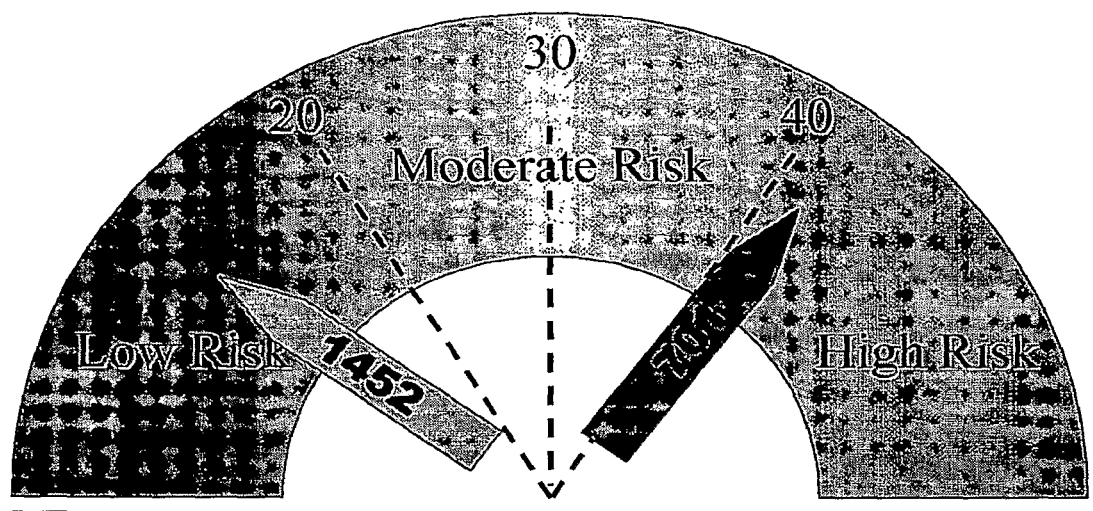
FIG. 7: Schematic representation of a display (Variability Gauge, Version 1) based on the ADRR and its categories, illustrated by the ADRR values of two subjects who had exactly the same average glycemia (HbA1c=8.0 for both).

7. Display of Variability Information:

FIG. 7 presents a possible display of the ADRR that could be used to create a "Variability Gauge" implemented in devices or software. The display is illustrated by the ADRR values of two subjects who had exactly the same average glycemia (HbA1c=8.0 for both), but very different glucose variability.

Figure 8:
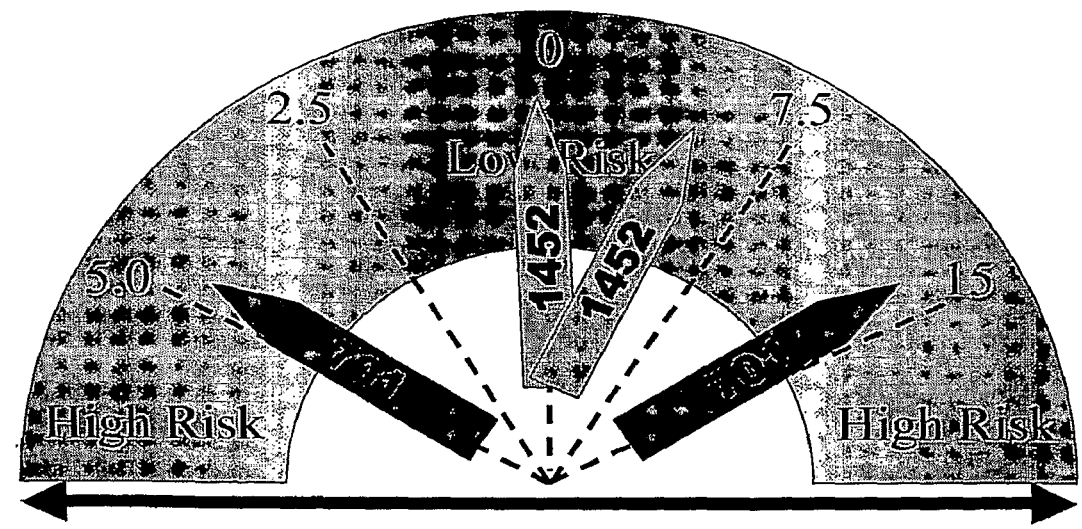
FIG. 8: Schematic representation of a display (Variability Gauge, Version 2) based on the LBGI and the HBGI and their categories, presenting separate risk values for hypoglycemia and hyperglycemia, and illustrated by the values of two subjects who had exactly the same average glycemia (HbA1c=8.0 for both)

FIG. 8 presents a possible display of the LBGI and HBGI that could be used to create a more detailed "Variability Gauge, Version 2" presenting separate information about the risk for hypoglycemia and hyperglycemia. The display is illustrated by the values of the same subjects #1452 and #701 whose data was used in FIG. 7.

FIGS. 7 and 8 send a notable clinical message summarized in Table 6: Despite their equivalent average glycemia these two people had very different glucose variability captured by the ADRR and the LBGI/HBGI combination. The difference in these subjects' glucose variability was the major reason for a dramatic disparity in their prospectively observed significant hypoglycemic and hyperglycemic episodes:

TABLE 6

| | Baseline Measures | | Prospective extreme glycemic episodes during the subsequent 3 months of observation | |
|---|---|---|---|---|
| | Average Glycemia | Glucose Variability | | |
| | HbA1c | ADRR | LBGI/HBGI | BG < 39 mg/dl | BG > 400 mg/dl |
| Subject # 1452 | 8.0 | 13.4 | 0.2/5.4 | 0 | 0 |
| Subject # 701 | 8.0 | 41.7 | 4.8/12.3 | 13 | 12 |

Post-hoc regression analyses were used to establish the relative contribution of average glycemia (HbA1c), ADRR, LBGI and HBGI towards prediction of future extreme glycemic episodes. The results indicated that the ADRR was the major predictor of future extreme low (BG<39 mg/dl)+ high (BG>400 mg/dl) episodes, accounting for 47.4% of their variance. HbA1c contributed an additional 7.8% to this prediction. The major predictor of future significant hypoglycemia was the LBGI, accounting for 44% of the variance of future episodes, while HbA1c contributed less than 1.5% to this prediction. The major predictor of future significant hyperglycemia was the HBGI, accounting for 48.4% of the variance of future episodes, while HbA1c contributed less than 0.6% to this prediction.

Figure 9:
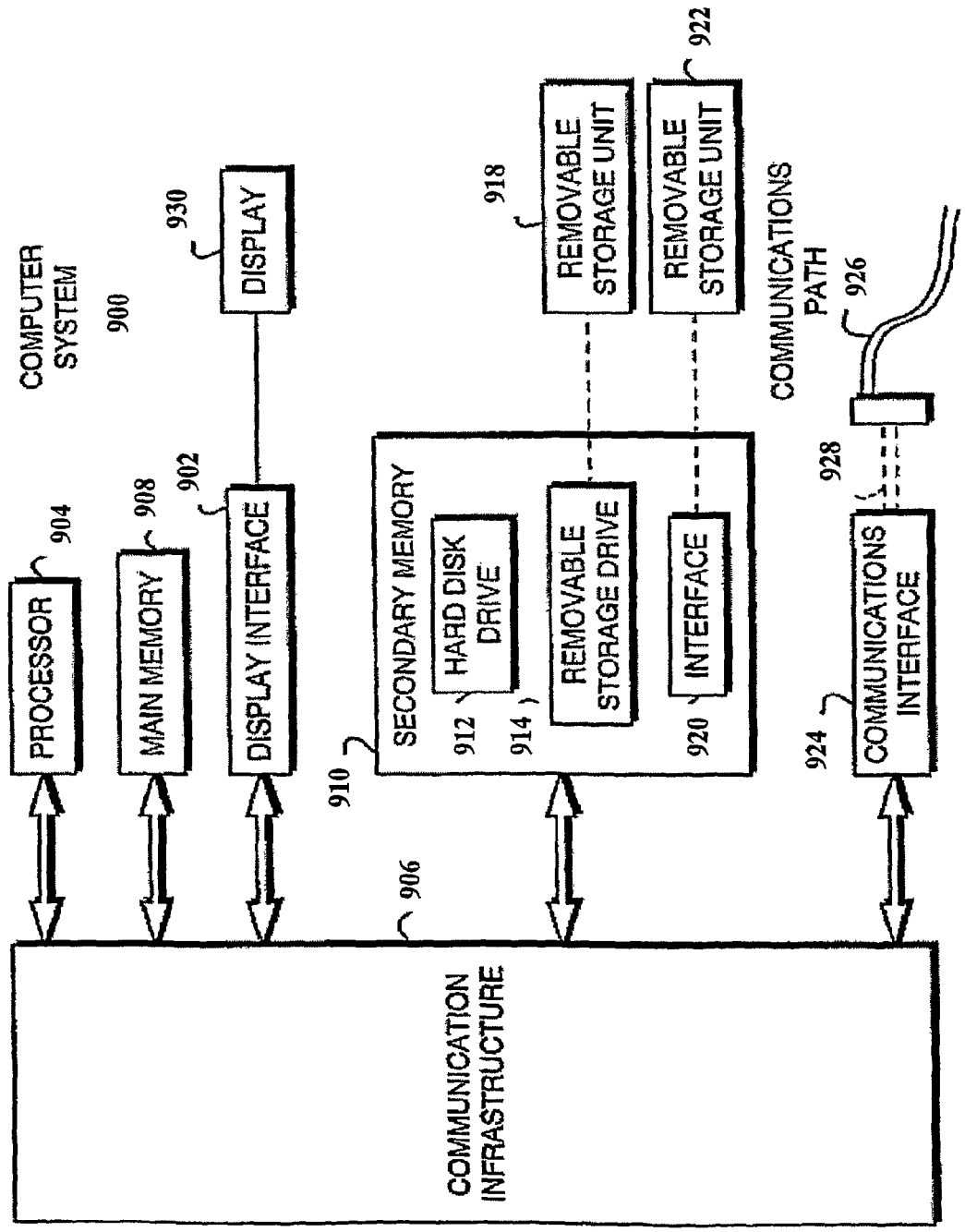
FIG. 9: Functional block diagram for a computer system for implementation of embodiments of the present invention.

8. Exemplary Systems: The method of the invention may be implemented using hardware, software or a combination thereof and may be implemented in one or more computer systems or other processing systems, such as a personal digital assistance (PDAs), or directly in blood glucose self-monitoring devices (e.g. SMBG memory meters) equipped with adequate memory and processing capabilities. In an example embodiment, the invention may be implemented in software running on a general purpose computer 900 as illustrated in FIG. 9. Computer system 900 may include one or more processors, such as processor 904. Processor 904 may be connected to a communications infrastructure 906 (e.g. a communications bus, cross-over bar, or network). Computer system 900 may include a display interface 902 that forwards graphics, text, or other data from the communications infrastructure 906 (or from a frame buffer not shown) for display on the display unit 930. Display unit 930 may be digital and/or analog.

Computer system 900 may also include a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, a flash memory, etc. The removable storage drive 914 reads from and/or writes to a removable storage unit 918 in a well known manner. Removable storage unit 918, represents a floppy disk, magnetic tape, optical disc, etc. which is read by and written to by removable storage drive 914. As will be appreciated, the removable storage unit 918 may include a computer usable storage medium having stored therein computer software and/or data.

In alternative embodiments, secondary memory 910 may include other means for allowing computer programs or other instructions to be loaded into computer system 900. Such means may include, for example, a removable storage unit 922 and an interface 920. Examples of such removable storage units/interfaces include a program cartridge and cartridge interface (such as that found in video game devices), a removable memory chip (such as a ROM, PROM, EPROM or EEPROM) and associated socket, and other removable storage units 922 and interfaces 920 which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port (e.g., serial or parallel, etc.), a PCMCIA slot and card, etc. Software and data transferred via communications interface 924 may be in the form of signals 928 which may be electronic, electromagnetic, optical or other signals capable of being received by communications interface 924. Signals 928 may be provided to communications interface 924 via a communications path (i.e., channel) 926. Channel 926 carries signals 928 and may be implemented using wire or cable, fiber optics, a phone line, a cellular phone link, an RF link, an infrared link, and other communications channels.

In this document, the terms "computer program medium" and "computer usable medium" are used to generally refer to media such as removable storage drive 914, a hard disk installed in hard disk drive 912, and signals 928. These computer program products are means for providing software to computer systems 900. The invention includes such computer program products.

Computer programs (also called computer control logic) may be stored in main memory 908 and/or secondary memory 910. Computer programs may also be received via communications interface 924. Such computer programs, when executed, enable computer system 900 to perform the features of the present invention as discussed herein. In particular, the computer programs, when executed, enable processor 904 to perform the functions of the present invention. Accordingly, such computer programs represent controllers of computer system 900. In an embodiment where the invention is implemented using software, the software may be stored in a computer program product and loaded into computer system 900 using removable storage drive 914, hard drive 912 or communications interface 924. The control logic (software), when executed by the processor 904, causes the processor 904 to perform the function of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language, but could be implemented in other programs, such as, but not limited to, C++ program language or other programs available to those skilled in the art.

Figure 10:
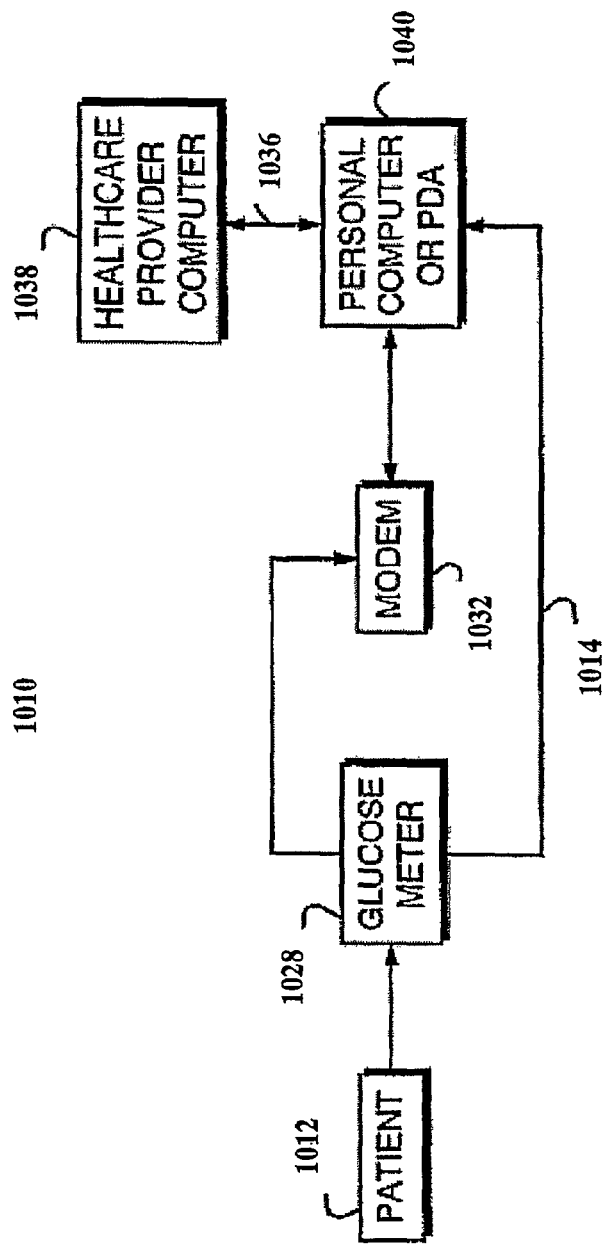
FIG. 10: Schematic block diagram for an alternative variation of an embodiment of the present invention relating processors, communications links, and systems.
Figure 11:
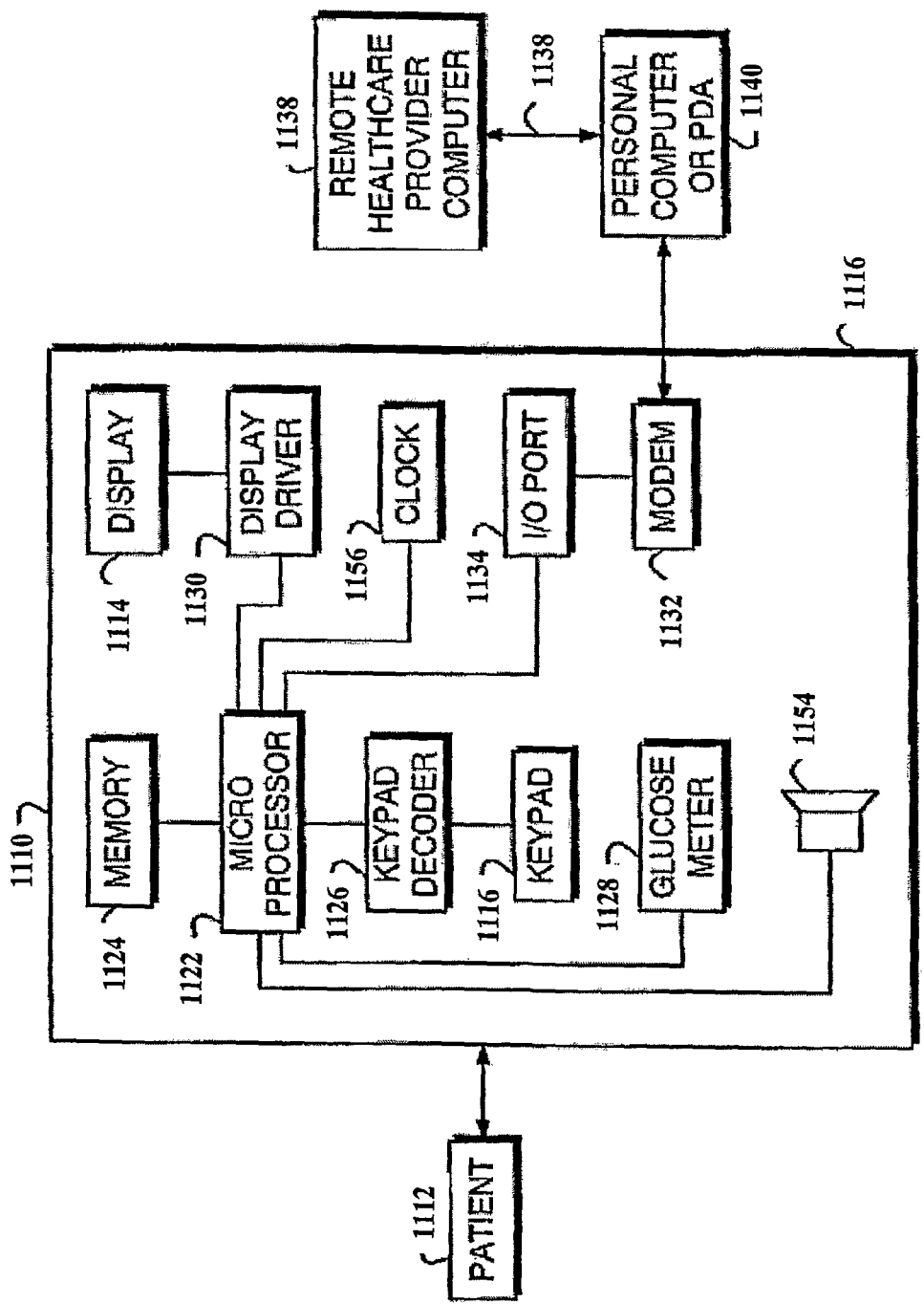
FIG. 11: Schematic block diagram for another alternative variation of an embodiment of the present invention relating processors, communications links, and systems.
Figure 12:
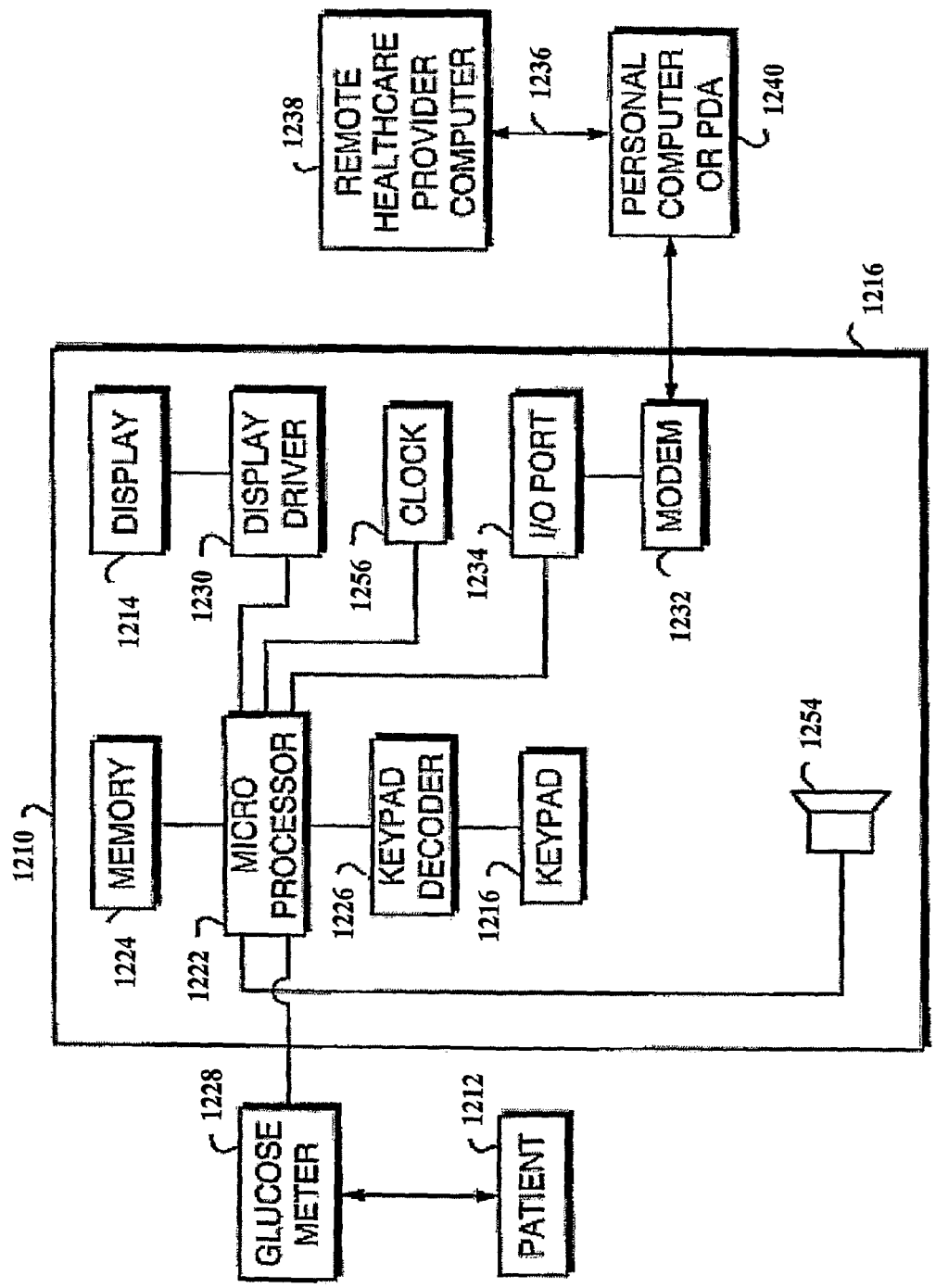
FIG. 12: Schematic block diagram for a third alternative variation of an embodiment of the present invention relating processors, communications links, and systems.

FIGS. 10-12 show block diagrammatic representations of alternative embodiments of the invention. Referring to FIG. 10, there is shown a block diagrammatic representation of the system 1010 essentially comprises the glucose meter 1028 used by a patient 1012 for recording, inter alia, insulin dosage readings and measured blood glucose ("BG") levels. Data obtained by the glucose meter 1028 is preferably transferred through appropriate communication links 1014 or data modem 1032 to a processor, processing station or chip 1040, such as a personal computer, PDA, or cellular telephone, or via appropriate Internet portal. For instance data stored may be stored within the glucose meter 1028 and may be directly downloaded into the personal computer 1040 through an appropriate interface cable and then transmitted via the Internet to a processing location. An example is the ONE TOUCH monitoring system or meter by LifeScan, Inc. which is compatible with IN TOUCH software which includes an interface cable to download the data to a personal computer. It should be appreciated that the glucose meter 1028 and any of the computer processing modules or storage modules may be integral within a single housing or provided in separate housings.

The glucose meter is common in the industry and includes essentially any device that can function as a BG acquisition mechanism. The BG meter or acquisition mechanism, device, tool or system includes various conventional methods directed towards drawing a blood sample (e.g. by fingerprick) for each test, and a determination of the glucose level using an instrument that reads glucose concentrations by electromechanical methods. Recently, various methods for determining the concentration of blood analytes without drawing blood have been developed. For example, U.S. Pat. No. 5,267,152 to Yang et al. (hereby incorporated by reference) describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al. (of which are hereby incorporated by reference).

U.S. Pat. No. 5,139,023 to Stanley (hereby incorporated by reference) describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich (hereby incorporated by reference) describes a passive glucose monitor that collects perspiration through a skin patch, where a cholinergic agent is used to stimulate perspiration secretion from the ecerine sweat gland. Similar perspiration collection devices are described in U.S. Pat. No. 5,076,273 to Schoendorfer and U.S. Pat. No. 5,140,985 to Schroeder (of which are hereby incorporated by reference).

In addition, U.S. Pat. No. 5,279,543 to Glikfeld (hereby incorporated by reference) describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Moreover, International Publication No. WO 96/00110 to Tamada (hereby incorporated by reference) describes an iotophoretic apparatus for transdermal monitoring of a target substance, wherein an iotophoretic electrode is used to move an analyte into a collection reservoir and a biosensor is used to detect the target analyte present in the reservoir. Finally, U.S. Pat. No. 6,144,869 to Berner (hereby incorporated by reference) describes a sampling system for measuring the concentration of an analyte present.

Further yet, the BG meter or acquisition mechanism may include indwelling catheters and subcutaneous tissue fluid sampling.

The computer or PDA 1040 may include the software and hardware necessary to process, analyze and interpret the self-recorded diabetes patient data in accordance with predefined flow sequences and generate an appropriate data interpretation output. The results of the data analysis and interpretation performed upon the stored patient data by the computer 1040 may be displayed in the form of a paper report generated through a printer associated with the personal computer 940. Alternatively, the results of the data interpretation procedure may be directly displayed on a video display unit associated with the computer 940. The results additionally may be displayed on a digital or analog display device. Preferably, the results may be displayed according to the characteristics presented in FIG. 7 or 8. The personal computer 1040 may transfer data to a healthcare provider computer 1038 through a communication network 1036. The data transferred through communications network 1036 may include the self-recorded diabetes patient data or the results of the data interpretation procedure.

FIG. 11 shows a block diagrammatic representation of an alternative embodiment having a diabetes management system that is a patient-operated apparatus 1110 having a housing preferably sufficiently compact to enable apparatus 1110 to be hand-held and carried by a patient. A strip guide for receiving a blood glucose test strip (not shown) is located on a surface of housing 1116. Test strip receives a blood sample from the patient 1112. The apparatus may include a microprocessor 1122 and a memory 1124 connected to microprocessor 1122. Microprocessor 1122 is designed to execute a computer program stored in memory 1124 to perform the various calculations and control functions as discussed in greater detail above. A keypad 1116 may be connected to microprocessor 1122 through a standard keypad decoder 1126. Display 1114 may be connected to microprocessor 1122 through a display driver 1130. Display 1114 may display the characteristics featured in FIG. 7 or 8. Display 1114 may be digital and/or analog. Speaker 1154 and a clock 1156 also may be connected to microprocessor 1122. Speaker 1154 operates under the control of microprocessor 1122 to emit audible tones alerting the patient to possible future hypoglycemic or hyperglycemic risks. Clock 1156 supplies the current date and time to microprocessor 1122.

Memory 1124 also stores blood glucose values of the patient 1112, the insulin dose values, the insulin types, and the parameters used by the microprocessor 1122 to calculate future blood glucose values, supplemental insulin doses, and carbohydrate supplements. Each blood glucose value and insulin dose value may be stored in memory 1124 with a corresponding date and time. Memory 1124 is preferably a non-volatile memory, such as an electrically erasable read only memory (EEPROM).

Apparatus 1110 may also include a blood glucose meter 1128 connected to microprocessor 1122. Glucose meter 1128 may be designed to measure blood samples received on blood glucose test strips and to produce blood glucose values from measurements of the blood samples. As mentioned previously, such glucose meters are well known in the art. Glucose meter 1128 is preferably of the type which produces digital values which are output directly to microprocessor 1122. Alternatively, blood glucose meter 1128 may be of the type which produces analog values. In this alternative embodiment, blood glucose meter 1128 is connected to microprocessor 1122 through an analog to digital converter (not shown).

Apparatus 1110 may further include an input/output port 1134, preferably a serial port, which is connected to microprocessor 1122. Port 1134 may be connected to a modem 1132 by an interface, preferably a standard RS232 interface. Modem 1132 is for establishing a communication link between apparatus 1110 and a personal computer 1140 or a healthcare provider computer 1138 through a communication network 1136. Specific techniques for connecting electronic devices through connection cords are well known in the art. Another alternative example is "Bluetooth" technology communication.

Alternatively, FIG. 12 shows a block diagrammatic representation of an alternative embodiment having a diabetes management system that is a patient-operated apparatus 1210, similar to the apparatus as shown in FIG. 11, having a housing preferably sufficiently compact to enable the apparatus 1210 to be hand-held and carried by a patient. For example, a separate or detachable glucose meter or BG acquisition mechanism/module 1228. There are already self-monitoring devices that are capable of directly computing the algorithms disclosed in this application and displaying the results to the patient without transmitting the data to anything else. Examples of such devices are ULTRA SMART by LifeScan, Inc., Milpitas, Calif. and FREE-STYLE TRACKER by Therasense, Alameda, Calif.

Accordingly, the embodiments described herein are capable of being implemented over data communication networks such as the internet, making evaluations, estimates, and information accessible to any processor or computer at any remote location, as depicted in FIGS. 9-12 and/or U.S. Pat. No. 5,851,186 to Wood, of which is hereby incorporated by reference herein. Alternatively, patients located at remote locations may have the BG data transmitted to a central healthcare provider or residence, or a different remote location.

It should be appreciated that any of the components/modules discussed in FIGS. 9-12 may be integrally contained within one or more housings or separated and/or duplicated in different housings.

It should also be appreciated that any of the components/modules present in FIGS. 9-12 may be in direct or indirect communication with any of the other components/modules.

In summary, the various embodiments of the invention propose a data analysis computerized (or non-computerized) method and system for the evaluation of the most important component of glycemic control in individuals with diabetes: glycemic variability. The method, while using only routine SMBG data, provides, among other things, an average daily risk range.

The potential implementations of the method, system, and computer program product of the various embodiments of the invention provide the following advantages, but are not limited thereto. First, the various embodiments of the invention enhance existing SMBG devices by introducing an intelligent data interpretation component capable of evaluating the extent, and predicting the risk of extreme BG fluctuations. They farther enable future SMBG devices by the same features.

As an additional advantage, the various embodiments of the invention enhance hand-held devices (e.g. PDAs) intended to assist diabetes management.

Still yet another advantage, the various embodiments of the invention enhance software that retrieves SMBG data. This software can reside on patients' personal computers, or be used via Internet portal.

Moreover, another advantage, the various embodiments of the invention may evaluate the effectiveness of various treatments for diabetes (e.g. insulin or variability lowering medications, such as pramlintide and exenatide).

Further still, the various embodiments of the invention may evaluate the effectiveness of new insulin delivery devices (e.g. insulin pumps), or of future closed-loop diabetes control systems.

Further still, the ADRR was developed using archival SMBG data from our previous studies. Then the measure was validated with a large data set, independently collected by LifeScan, which confirmed the initial analyses. Thus, we can assume that the ADRR was appropriately tested and validated. Previously introduced measures, the LBGI and the HBGI, were re-validated with the new data as well. Given the results of the comparison of the predictive value of the ADRR, LBGI, and HBGI vs. other measures of glycemic variability, we can conclude that:
1) The ADRR is the best overall measure of glycemic variability;
2) The ADRR is predictive of both future extreme hypoglycemic and hyperglycemic events over various time horizons, accounting for nearly 50% of their variance;
3) Separately in the hypoglycemic and hyperglycemic ranges, LBGI and the HBGI are consistently among the best variability measures. Because the LBGI and the HBGI are designed to be complementary to each other, the pair LBGI/HBGI is a better representation of overall glycemic variability than any other combination of measures presented in Tables 4A, 4B, and 4C;
4) The ADRR, as well as the combination LBGI/HBGI, have independent from average glycemia contribution to the prediction of extreme glycemic excursions. In fact, the major responsibility for future extreme episodes is carried by glucose variability, not by average glycemia.

The following references and applications (and which were cited throughout this document) are hereby incorporated by reference herein in their entirety:
1. Aaby Svendsen P, Lauritzen T, Soegard U, Nerup J. *Diabetologia,* 23: 403-405, 1982.
2. American Diabetes Association. Postprandial Blood Glucose: Consensus Statement. *Diabetes Care* (2001) 24: 775-778.
3. Amiel S A, Sherwin R S, Simonson D C, Tamborlane W V. *Diabetes* 37: 901-907, 1988
4. Amiel, S A, Tamborlane, W V, Simonson, D C and Sherwin, R S. *N Engl J Med* 316: 1376-1383, 1987
5. Anderson S M, Clarke W L, Cox D J, Gonder-Frederick, L A, and Kovatchev B P. *Diabetes,* 53, Supplement 2: A485.
6. Bergman R N, Ider Y Z, Bowden C R, Cobelli C (1979). *Am J Physiol.* 236:E667-E677.
7. Clark A D H, Youd J M, Rattigan S, Barrett E J, Clark MG. *Am J Physiol;* 280:H1324-H1333, 2001.
8. Clark M G, Wallis M G, Barrett E J, Vincent M A, Richards S M, Clerk L H, Rattigan S. *Am J Physiol Endocrinol Metab* 284:E241-E258, 2003
9. Clerk L H, Vincent M A, Lindner J R, Clark M G, Rattigan S, Barrett E J. *Diabetes Metab Res Rev,* 20: 3-12, 2004.
10. Cox D J, Gonder-Frederick L A, Antoun B, Cryer P, Clarke W L. *Diabetes Care,* 16: 519-527, 1993.

11. Cox D J, Gonder-Frederick L A, McCall A, et al. *International Journal of Clinical Practice* (2002) Supplement 129: 20-26.
12. Cox D J, Kovatchev B, Julian D, Gonder-Frederick L A, Polonsky W H, Schlundt D G, Clarke W L. *Journal of Clinical Endocrinology and Metabolism* 79: 1659-1662, 1994.
13. Cox D J, Kovatchev B P, Gonder-Frederick L A, Summers K H, McCall A, Grimm K J, Clarke W L (2005). *Diabetes Care*, 28: 71-77.
14. Cox D J, Kovatchev B P, Gonder-Frederick L A, Clarke W L (2003). *Canadian J of Diabetes*, 27:23-28.
15. Cryer P E, Davis S N, Sharnoon H. *Diabetes Care*, 26: 1902-1912, 2003
16. Cryer P E, *Diabetes*, 43: 1378-1389, 1994
17. Cryer P E, Gerich J E. *N Engl J Med* 313: 232-241, 1985
18. Cryer P E. *Diabetes* 42:1691-1693, 1993
19. Cryer P E. *Diabetologia* 45: 937-948, 2002
20. Dagogo-Jack S E, Craft S, Cryer P E *J Clin Invest* 91:819-828, 1993
21. Dawson D, Vincent M A, Barrett E J, Kaul S, Clark A, Leong-Poi H, Lindner J R. *Am J Physiol Endocrinol Metab*, 282: E714-E720, 2002.
22. De Sonnaville J J, Snoek F J, Colly L P, et al. *Diabetes Care* (1998) 21: 919-924.
23. DeFronzo R A, Tobin J D, Andres R. *Amer J Physiol* 237, E214-23, 1979
24. DIGAMI Study Group, Malmberg K, Ryden L, Efendic S, Herlitz J, Nicol P, Waldenstrom A, Wedel H, Welin L. *J Am Coll Cardiol* 26: 57-65, 1995
25. Esposito K, Giugliano D, Nappo F, Martella K, for the Campanian Postprandial Hyperglyceria Study Group. Circulation 110: 214-219, 2004.
26. Feller W: An Introduction to Probability Theory and its Applications. Second Edition, Volume 1. New York, John Wiley & Sons, 1971.
27. Gacde P., Vedel P., Larsen N., Jensen G. V. H., Parving H., Pedersen O. (2003). *N Engl J Med.* 348:383-393.
28. Gavin J R 3rd. *International Journal of Clinical Practice* (1999) Supplement 107: 14-17.
29. Gold A E, Frier B M, MacLeod K M, Deary I J. *Diabet Med* 14:309-315, 1997
30. Haffner S. M., Lehto S., Rönnemaa T., Pyörälä K., Laakso M. (1998) *N Engl J Med*, 339:229-234.
31. Haffner S. M., *International Journal of Clinical Practice* (2001) Supplement 123: 24-26.
32. Hanefeld M, Fisher S, Julius U. *Diabetologia* (1996) 39: 1577-1583.
33. Hanefeld M. *International Journal of Clinical Practice* (2000) Supplement 112: 13-18.
34. Hanefeld M. *International Journal of Clinical Practice* (2002) Supplement 129: 45-50.
35. Hanefeld M. Temelkova-Kurktschiev T. *Diabetic Medicine* (1997) 14 Supplement 3: S6-11.
36. Henderson J N, Allen K V, Deary I J, Frier B M. *Diabet Med* 20: 1016-1021, 2003
37. Hirsh I B, Brownlee M. *J Diabetes Complications* 19:178-181, 2005
38. Honig C R, Odoroff C L, Frierson J L (1982) *Am. J. Physiol*, 243 (Heart Circ. Physiol. 12): H196-H206, 1982.
39. Kovatchev B P, Cox D J, Farhy L S, Straume M, Gonder-Frederick L A, Clarke, W L. *J Clin Endocrinol Metab* 85:4287-4292, 2000
40. Kovatchev B P, Cox D J, Gonder-Frederick L A and W L Clarke. *Diabetes Care* 20:1655-1658, 1997.
41. Kovatchev B P, Cox D J, Gonder-Frederick L A and W L Clarke. *Diabetes Technology and Therapeutics*, 4: 295-303, 2002.
42. Kovatchev B P, Cox D J, Gonder-Frederick L A Young-Hyman D, Schlundt D, Clarke W L, *Diabetes Care* 21: 1870-1875, 1998
43. Kovatchev B P, Cox D J, Gonder-Frederick L A, Clarke W L (2003), *Diabetologia*, 46, Suppl 2, A304.
44. Kovatchev B P, Cox D J, Gonder-Frederick L A, Schlundt D and W L Clarke. (1998) *Health Psychology*, 17:277-284.
45. Kovatchev B P, Cox D J, Kumar A, Gonder-Frederick L A and W L Clarke. *Diabetes Technology and Therapeutics*, 5 (5): 817-828, 2003
46. Kovatchev B P, Cox D J, Su mers KH, Gonder-Frederick L A, Clarke W L. *J of Applied Research*, 3 (4): 449-458, 2003
47. Kovatchev B P, Straume M, Cox D J, Farhy L S (2001). *J of Theoretical Medicine*, 3:1-10, 2001.
48. Kovatchev B P, Straume M, Farhy L S, Cox D J. (2000). In: Methods in Enzymology, vol. 321: Numerical Computer Methods, Part C:396-410 M. Johnson & L. Brand, Eds., Academic Press, NY.
49. Kovatchev B P & Cox D J (2001). Method, system, and computer program product for the evaluation of glycemic control in diabetes from self-monitoring data, PCT/US01/09884; World Intellectual Property Organization, No. WO 01/72208, and corresponding U.S. application Ser. No. 10/240,228 and Divisional Application thereof U.S. application Ser. No. 11/305,946.
50. Kovatchev B P & Cox D J (2003). Method, system, and computer program product for processing of self-monitoring blood glucose (SMBG) data to enhance diabetic self-management, PCT/US2003/25053; World Intellectual Propert=Organization, No. WO 2004/015539, and corresponding U.S. application Ser. No. 10/524,094.
51. Malmberg K, Ryden L, Wedel H, Birkeland K, Bootsma A, Dickstein K, Efendic S, Fisher M, Hamsten A, Herlitz J, Hildebrandt P, MacLeod K, Laakso M, Torp-Pedersen C, Waldenstrom A for the DIGAMI (2005). *Eur Heart J* 26: 650-661.
52. Quagliaro L, Piconi L, Assalone R, Martinelli L, Motz E, Ceriello A. *Diabetes* 52: 2795-2804, 2003.
53. Rattigan S, Clark M G, Barrett E J. *Diabetes*, 48: 564-569, 1999.
54. Reichard P, Phil M. *Diabetes*, 43: 313-317, 1994
55. Ryan E A, Shandro T, Green K, Paty B W, Senior P A, Bigam D, Shapiro A M J, Vantyghem M C. *Diabetes* 53: 955-962, 2004
56. Santiago J V. Lessons from the Diabetes Control and Complications Trial, *Diabetes*, 42:1549-1554, 1993.
57. Schlichtkrull J, Munck O, Jersild M. *Acta Med Scand* 177: 95-102, 1965
58. Segel S A, Paramore D S, Cryer P E. *Diabetes* 51: 724-733, 2002
59. Service F J, Molner G D, Rosevear J W, Ackerman E, Gatewood L C, Taylor W F. *Diabetes* 19: 644-655, 1970
60. The Diabetes Control and Complications Trial Research Group. *Diabetes* 46: 271-286, 1997
61. The Diabetes Control and Complications Trial Research Group. *N Engl J Med* 329: 978-986, 1993
62. UK Prospective Diabetes Study Group (UKPDS). *Lancet* 352: 837-853, 1998
63. Van der Does F E. De Neeling T N, Snoek F J et al. *Diabetes Care* (1996) 19: 204-210.
64. Vincent M A, Dawson D, Clark AD et al. *Diabetes* 51: 42-48, 2002

65. Wallis M G, Wheatley C M, Rattigan S, Barrett E J, Clark A D, Clark M G. *Diabetes;* 51(12):3492-8, 2002
66. Ward G M, Weber K M, Walters I M, Aitken P M, Lee B, Best J D, Boston R C and Alford F P (1991). *Metabolism* 40: 4-9.
67. Weber K, Martin I K, Best J D, et al (1989). *Am J Physiol* 256: E524-535.
68. White N H, Skor D A, Cryer P E, Levandoski L, Santiago J V. *N Engl J Med* 308:485-491, 1983
69. Wolever T M S, Palmason C, Chiasson J et al. *Diabetes Care* (1998) 21: 336-340.

The following publications are also incorporated by reference herein in their entirety:

1. Kovatchev B P, Cox D J, Gonder-Frederick L A and W L Clarke (1997). Symmetization of the Blood Glucose Measurement Scale and Its Applications, *Diabetes Care,* 20, 1655-1658.
2. Kovatchev B P, Cox D J, Gonder-Frederick L A Young-Hyman D, Schlundt D and W L Clarke (1998). Assessment of Risk for Severe Hypoglycemia Among Adults with IDDM: Validation of the Low Blood Glucose Index, *Diabetes Care,* 21: 1870-1875.
3. Kovatchev B P, Straume M, Cox D J, Farhi L S (2001) Risk Analysis of Blood Glucose Data: A Quantitative Approach to Optimizing the Control of Insulin Dependent Diabetes. *J of Theoretical Medicine,* 3: 1-10.
4. Kovatchev B P, Cox D J, Gonder-Frederick L A and W L Clarke (2002). Methods for quantifying self-monitoring blood glucose profiles exemplified by an examination of blood glucose patterns in patients with Type 1 and Type 2 Diabetes. *Diabetes Technology and Therapeutics,* 4 (3): 295-303.
5. Kovatchev B P, Cox D J, Kumar A, Gonder-Frederick L A, Clarke W L (2003). Algorithmic Evaluation of Metabolic Control and Risk of Severe Hypoglycemia in Type 1 and Type 2 Diabetes Using Self-Monitoring Blood Glucose (SMBG) Data. *Diabetes Technology and Therapeutics,* 5 (5): 817-828.

In summary, Glycosylated hemoglobin ($HbA_{1c}$) is the classic marker of average glycemic control in diabetes, introduced 23 years ago, linked to long-term complications of diabetes, and confirmed as the gold standard for both Type 1 and Type 2 diabetes mellitus (T1DM, T2DM). However, HbA1c is a measure of average glycemia that is insensitive to the magnitude and variability of blood glucose (3G) fluctuations. However, recent studies show the importance of controlling BG variability, particularly in relationship to reducing instances of hypoglycemia at the low end of the BG scale and attenuating the risk for cardiovascular disease and behavioral complications at the high end of the BG scale. Thus, providing accurate feedback about BG variability would improve patient's self-treatment practices and reduce risk of serious diabetes-related complications.

The various embodiments of the present invention comprise a new system and method for quantifying BG variability from routine episodic self-monitoring BG (SMBG) data. The method is based on, but not limited thereto, our previously developed theory of risk analysis of BG data and includes the computing of a new measure—the Average Daily Risk Range (ADRR) of glucose fluctuations. In an investigation involving over 300 people with diabetes, the ADRR proved to be superior to other known measures (standard deviation of BG, counting of hypo- and hyperglycemic events, M-value, MAGE, Liability Index, etc.) in evaluating BG variability and predicting future significant hypoglycemic and hyperglycemic events. In contrast to all other known measures, the ADRR is equally sensitive (by design and as proven by data) to both hypoglycemia and hyperglycemia.

Accordingly, the ADRR is a most effective currently available measure of glycemic variability in diabetes and the only available measure that is equally sensitive to both hypoglycemic and hyperglycemic excursions.

Blood glucose self-monitoring devices are the current standard observational practice in diabetes, providing routine SMBG data that serve as the main feedback enabling patients to maintain their glycemic control. The various embodiments of the present invention has, but not limited thereto, the following exemplary SMBG-related applications:

Provide accurate evaluation of one of the most important parameters of diabetes control—glucose variability by way of a field test based on routine self-monitoring (SMBG) data;

Forecast variability-related diabetes complications, such as acute hypoglycemic events and chronic cardiovascular complications;

Serve as a measure for assessment the effectiveness of medications reducing glucose variability in diabetes (such as pramlintide, Amylin Pharmaceuticals, San Diego, Calif.);

Serve as a measure for assessment the effectiveness of insulin therapies targeting the reduction of glucose variability.

Some advantages of the Average Daily Risk Range over these existing measures include for example, but not limited thereto, the following: (i) Equal sensitivity to hypoglycemic and hyperglycemic variation; (ii) Better ability to predict future significant hypoglycemic or hyperglycemic events; and (iii) Clinically-relevant risk perception of the ADRR estimates based on the risk-space interpretation of glucose fluctuations.

It should be appreciated that various aspects of embodiments of the present method, system and computer program product may be implemented with the following methods, systems and computer program products disclosed in the following U.S. patent applications, U.S. patents, and PCT International Patent Applications that are hereby incorporated by reference herein and co-owned with the assignee:

International Application No. PCT/US2005/013792, filed Apr. 21, 2005, entitled "Method, System and Computer Program Product for Evaluating the Accuracy of Blood Glucose Monitoring Sensors/Devices;"

U.S. patent application Ser. No. 11/578,831, filed Oct. 18, 2006, entitled "Method, System and Computer Program Product for Evaluating the Accuracy of Blood Glucose Monitoring Sensors/Devices;"

International Application No. PCT/US01/09884, filed Mar. 29, 2001, entitled "Method, System, and Computer Program Product for the Evaluation of Glycemic Control in Diabetes from Self-Monitoring Data;"

U.S. Pat. No. 7,025,425, issued Apr. 11, 2006, entitled "Method, System, and Computer Program Product for the Evaluation of Glycemic Control in Diabetes from Self-Monitoring Data;"

International Application No. PCT/US20031025053, filed Aug. 8, 2003, entitled "Method, System, and Computer Program Product for the Processing of Self-Monitoring Blood Glucose Data (SMBG) to Enhance Diabetic Self-management;"

U.S. patent application Ser. No. 10/524,094, filed Feb. 9, 2005 entitled, "Managing and Processing Self-Monitoring Blood Glucose;";

U.S. patent application Ser. No. 11/305,946, filed Dec. 19, 2005, entitled "Method, System, and Computer Program Product for the Evaluation of Glycemic Control in Diabetes from Self-Monitoring Data;" and International Application No. PCT/US06/033724, filed Aug. 29, 2006, entitled "Method for Improvising Accuracy of Continuous Glucose Sensors and a Continuous Glucose Sensor Using the Same."

Various aspects of the present invention method, system, and computer program product are now described with reference to the following examples providing select results and validation. These examples are provide for purpose of illustration only and the invention should in no way be construed as being limited to these examples, but rather should be construed to encompass any and all variations which become evident as a result of the teachings provided herein.

Example A

Relationship of Measures of Glucose Variability with Out of Control Glucose Results Background: Evidence is accumulating that glucose excursions may be a significant contributor to the complications in diabetes. In addition, glucose excursions must be minimized to optimally reduce HbA1c. Therefore there is a need to determine measures of glucose variability that can be used to manage and reduce glucose excursions.

Methods: Using a sample of one month of longitudinal time stamped self-monitoring of blood glucose (SMBG) data from a large dataset of 335 patients, different variability measures used in clinical practice and described in the literature including Standard Deviation (SD), Range, Mean Amplitude of Glycemic Excursion (MAGE), M-Value and the Liability Index were computed and related to the frequency of out of control glucose results (Glucose<70 mg/dl or Glucose>180 mg/dl) in the subsequent 1 month of patient SMBG results. SD and mean groupings for various HbA1c cohorts were also devised and related to frequency of out of control glucose results. Lastly, a new measure of variability developed by the University of Virginia called the Average Daily Risk Range (ADRR) was also evaluated. Variability measures were correlated with out of control glucose results, cross-tables of out-of-control glucose result categories, and chi-square analyses to check for power of association.

Results: SD and Mean groupings do not show clear predictability of out of control glucose results over whole HbA1c range but do show good relationship to frequency of out of control glucose results when done by HbA1c subgroups. As a single measure of variability, ADRR demonstrated better association with subsequent month out of control results than other variability measures tested.

Figure 13:
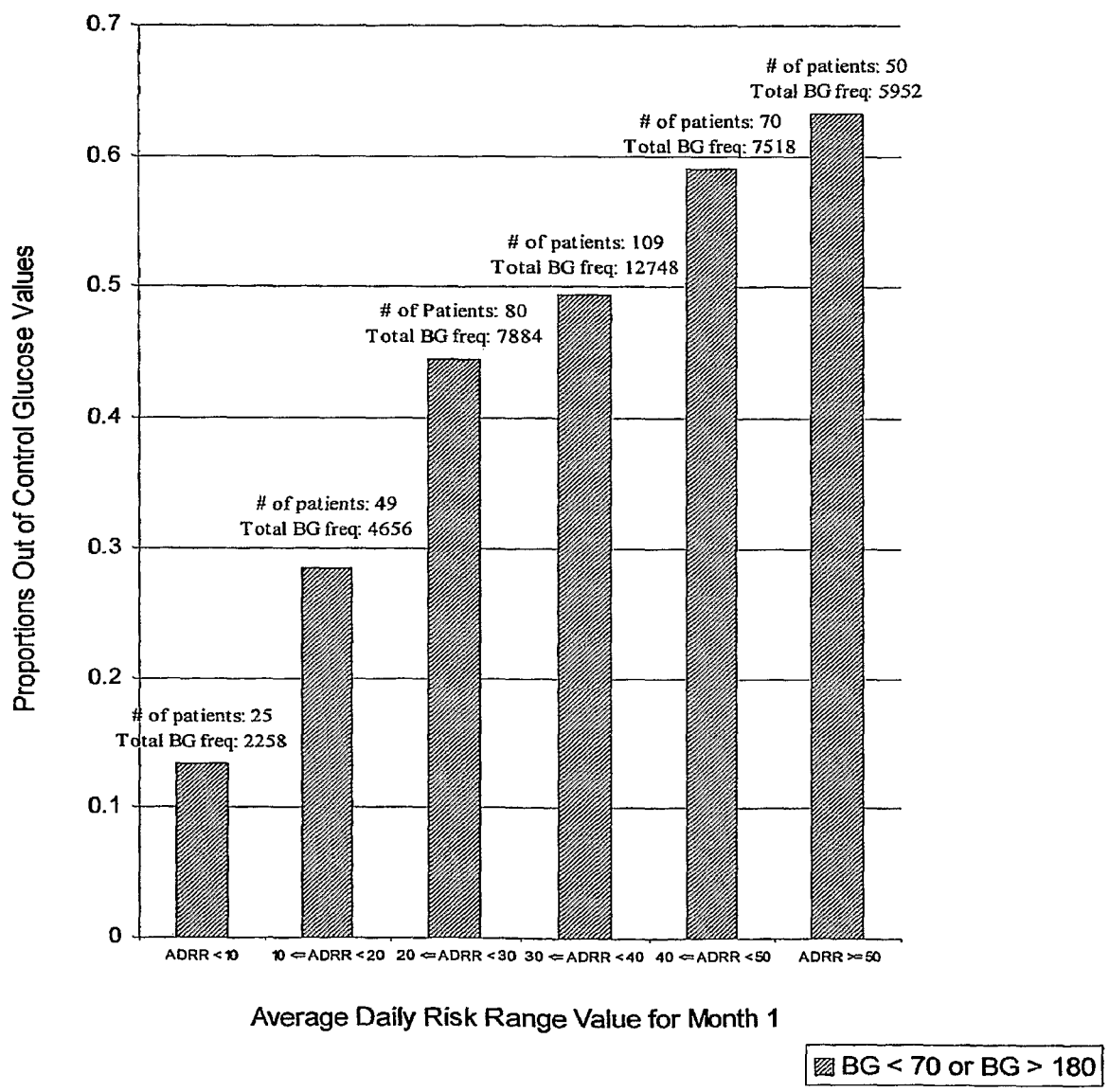
FIG. 13: Graphical representation of the association of ADRR with subsequent month's Out of Control Glucose results.

Conclusions: As demonstrated in FIG. 13, ADRR shows strong association with subsequent one month out of control glucose readings on a large patient database.

Example B

Algorithmic Design of an Intelligent Blood Glucose Meter Phase 4 Data File Description and Preliminary Results Introduction:

The data collection of Phase 4 was a continuation of a large NIH-funded study NIDDK RO1 DK 51562, "Bio-Behavioral Monitoring and Control of IDDM" with Principal Investigator Boris Kovatchev, specifically of the data from its Hospital-laboratory study (HIC #10714), which investigates metabolic parameters of adults with T1DM during hyperinsulinemic euglycemic clamp and subsequent descent into hypoglycemia with a target level of 40 mg/dl. During this study, metabolic demand and counterregulation data were collected for 39 people with T1DM. The computation of each person's individual metabolic demand (IMD) used the classic DeFronzo's clamp equations, modified by BK to account for non-steady states, such as exercise and hypoglycemia. Counterregulatory response was assessed by a direct measurement of epinephrine levels at baseline and then every 10 minutes during descent into hypoglycemia.

In addition, prior to their hospital study, most of the participants collected >2 months of SMBG data using LifeScan OneTouch Ultra meters. We will refer to this initial data set as baseline SMBG.

During Phase 4, thirty of the participants in the NIH study were re-enrolled in a 2-week follow-up using LifeScan UltraSmart meter to collect SMBG data 4-5 per day, as well as record data about carbohydrate intake, insulin doses, and physical activity.

A number of SMBG characteristics were computed from baseline and follow-up data as specified below, including average BG, standard deviation, Low and High BG Indices (LBGI, HBGI), and the new Variability Index—Average Daily Risk Range (ADRR).

The initial data set collected by NIH RO1 DK 51562 was merged with demographic data and with the data from the 2-week follow-up study to produce the results below. Descriptive statistics and exploratory correlations are given below. These preliminary analyses confirm that:

(1) The SMBG-derived parameters, LBGI, HBGI and ADRR, are reliable over time, even if the elapsed time between baseline and follow-up assessments is more than one year for most subjects;

(2) The SMBG-derived parameters, specifically the ADRR predict very well metabolic demand (IMD) and counterregulatory response (Epi) assessed in the hospital: the correlation of baseline ADRR and subjects' IMD (in mg/kg/minute) during euglycemia was 0.59, $p=0.002$; the correlation of the ADRR with peak epinephrine release during induced hypoglycemia was $-0.52$, $p=0.008$. Thus, increased glucose variability measured in subjects' natural environment is related to both increased glucose uptake and reduced counterregulatory response measured in a hospital study. This result is very important in view of the overall objective of Phase 4 to create a bolus calculator: It follows that the ADRR can be used as a field correlate of both insulin sensitivity and counterregulatory ability as measured by "gold-standard" laboratory assessments. No other measure of glucose variability achieved statistically significant relationship with these hospital parameters, which underscores the importance of measuring BG variability in risk space and the advantage of the ADRR.

(3) Significant relationships exist between SMBG and carb/insulin parameters in the follow-up data that will be investigated further to design a bolus calculator:

Description of the Data Files:
ID Subject ID number, identifying subjects across studies and data files;

| Demographic characteristics - file DEMO.XLS: | | | | | | |
|---|---|---|---|---|---|---|
| | Mean | S.D. | Minimum | Maximum | N | Units |
| AGE | 44.73 | 11.55 | 22 | 67 | 30 | Years |
| HEIGHT | 170.96 | 8.64 | 155.7 | 184.2 | 30 | cm |
| WEIGHT | 80.63 | 13.66 | 57.3 | 104.3 | 30 | kg |
| BMI | 27.64 | 4.73 | 21.6 | 40.1 | 30 | kg/m$^2$ |
| DIAG_AGE | 20.70 | 11.75 | 1 | 41 | 30 | Age at diagnosis |
| HBA1C | 7.35 | .81 | 5.9 | 9.0 | 30 | |
| SEX | 1 = male, 2 = female, N = 14 males | | | | | |
| RACE | 1 = white (N = 29), 2 = black | | | | | |

NIH Baseline SMBG Data - file NIH FIELD.XLS
(data available for N = 25 subjects):

| | |
|---|---|
| MBG0 | Average BG at baseline |
| SBG0 | S.D. of BG at baseline |
| NC0 | # SMBG readings during 2-month baseline observation |
| LBGI0 | baseline LBGI |
| HBGI0 | baseline HBGI |
| N39_0 | # SMBG readings <= 39 mg/dl during 2-month baseline observation |
| N400_0 | # SMBG readings >400 mg/dl during 2-month baseline observation |
| ADRR0 | baseline ADRR |

| | Mean | S.D. | Minimum | Maximum | N |
|---|---|---|---|---|---|
| MBG0 | 150.41 | 28.25 | 101.51 | 211.35 | 25 |
| SBG0 | 74.67 | 18.60 | 49.73 | 119.74 | 25 |
| NC0 | 314.92 | 159.04 | 41.00 | 611.00 | 25 |
| LBGI0 | 4.16 | 2.79 | .18 | 11.21 | 25 |
| HBGI0 | 7.84 | 4.28 | 1.98 | 19.23 | 25 |
| N39_0 | 8.00 | 14.62 | .00 | 63.00 | 25 |
| N400_0 | 2.28 | 4.35 | .00 | 19.00 | 25 |
| ADRR0 | 35.31 | 12.37 | 15.80 | 65.98 | 25 |

NIH Hospital Study Data - file NIH HOSP.XLS
(data available for N = 25 subjects):

| | |
|---|---|
| IMDBASE | IMD during steady-state euglycemia |
| IMDEX | IMD during exercise during euglycemia |
| EPIBASE | Epinephrine during euglycemia |
| EPIMAX | Max epinephrine during hypoglycemia - (usually Epi rise above 100 pg/l is considered a marker of counterregulatory response). |
| BGNADIR | Nadir of BG during hypoglycemia |

NIH Hospital Study Data - file NIH HOSP.XLS
(data available for N = 25 subjects):

| | Mean | S.D. | Minimum | Maximum | N | Units |
|---|---|---|---|---|---|---|
| IMDBASE | 4.08 | 2.30 | .3924 | 9.5521 | 30 | mg/kg/min |
| IMDEX | 6.25 | 3.24 | .8044 | 17.0180 | 30 | mg/kg/min |
| EPIBASE | 54.42 | 30.74 | 12 | 122 | 30 | pg/l |
| EPIMAX | 280.63 | 194.15 | 41 | 762 | 30 | pg/l |
| BGNADIR | 46.77 | 6.47 | 38 | 71 | 30 | mg/dl |

Phase 4 SMBG data - data at the level of meter entry are in file PHASE4.XLS (contains 12,121 entries). This dataset is organized by Subject ID, Day, and Hour, as follows:

| | |
|---|---|
| Day | Day of meter entry |
| Hour | Hour of meter entry |
| BG | Represents the Blood Glucose measurement if one was measured at that time and day. If no measurement was taken, it is left blank. |
| Carb | Represents a measurement of the carbohydrates consumed by the subject at that time and day. |

-continued

| | |
|---|---|
| Basal | If the subject has an insulin pump (N = 22 out of 30 subjects), Basal represents how much insulin they receive at that hour of the day. If the subject does not have an insulin pump, all values are set to Zero. |
| Bolus | If the subject is on insulin pump, Bolus is the recorded insulin correction. If the subject is not on a pump, it represents an insulin injection. |
| MildEx | The number of minutes a subject exercised mildly. |
| ModEx | The number of minutes a subject exercised moderately. |
| HardEx | The number of minutes the subject had rigorous exercise. |
| ADRR | The variability index value for the day. It is only shown on hour 23. It represents the sum of the Maximum HBGI and the Maximum LBGI |
| HBGI | The subject's riskHI value computed on the current BG reading. |
| LBGI | The subject's riskLO value computed on the current BG reading. |

Phase 4 SMBG data - data at the level of a person are in file PHASE4a.XLS

| | |
|---|---|
| ADRR | follow-up ADRR |
| LBGI | follow-up LBGI |
| HBGI | follow-up HBGI |
| MBG | follow-up average BG |
| SBG | follow-up SD of BG |
| NC | # SMBG readings at follow-up |
| CARB | average carbs |
| TOTINS | average total insulin |
| TOTINS1 | average total insulin per kilogram weight |
| BASAL | average basal insulin (for those who are on the pump, N = 22) |
| BASAL1 | average basal insulin per kilogram weight |
| BOLUS | average bolus (for those who are on the pump, N = 22) |
| BOLUS1 | average bolus per kilogram weight |

| | Mean | S.D. | Minimum | Maximum | N |
|---|---|---|---|---|---|
| ADRR | 31.73 | 9.55 | 13.41 | 58.88 | 30 |
| LBGI | 4.07 | 2.46 | .53 | 9.19 | 30 |
| HBGI | 6.46 | 3.81 | 1.69 | 18.29 | 30 |
| MBG | 158.72 | 29.52 | 117.39 | 246.03 | 30 |
| SBG | 77.05 | 15.96 | 52.39 | 117.19 | 30 |
| NC | 404.00 | 102.81 | 336.00 | 912.00 | 30 |
| CARB | 137.47 | 68.57 | 1.87 | 282.56 | 30 |
| TOTINS | 39.08 | 22.32 | .54 | 124.75 | 30 |
| INS_KG | .47 | .23 | .01 | 1.28 | 30 |
| BOLUS | 16.55 | 5.89 | 6.88 | 30.59 | 22 |
| BOLUS1 | .21 | .07 | .07 | .31 | 22 |
| BASAL | 21.70 | 9.61 | 3.60 | 43.20 | 22 |
| BASAL1 | .26 | .11 | .05 | .52 | 22 |

\* Insulin and carb entries for two subjects, #76 and 182 will need to be verified further.

Preliminary Results:
(1) Baseline vs. Follow-up reliability of SMBG-based measures is high as confirmed by the correlations below (all correlations are above 0.6):

|       | MBG              | SBG              | ADRR             | LBGI             | HBGI             |
|-------|------------------|------------------|------------------|------------------|------------------|
| MBG0  | .6158<br>P = .001 | .6202<br>P = .001 | −.0664<br>P = .752 | −.1979<br>P = .343 | .6321<br>P = .001 |
| SBG0  | .4713<br>P = .017 | .8161<br>P = .000 | .4130<br>P = .040 | .2100<br>P = .314 | .5785<br>P = .002 |
| ADRR0 | −.0723<br>P = .731 | .3259<br>P = .112 | .6052<br>P = .001 | .4750<br>P = .016 | .0473<br>P = .822 |
| LBGI0 | −.4105<br>P = .042 | −.0253<br>P = .904 | .4852<br>P = .014 | .6208<br>P = .001 | −.2855<br>P = .116 |
| HBGI0 | .5768<br>P = .003 | .7303<br>P = .000 | .0979<br>P = .641 | −.0053<br>P = .980 | .6430<br>P = .001 |

(2) The ADRR predicts very well metabolic demand (IMD) and counterregulatory response (Epi) assessed in the hospital:

|       | IMDBASE           | IMDEX             | EPIBASE           | EPIMAX            |
|-------|-------------------|-------------------|-------------------|-------------------|
| HBA1C | −.0451<br>P = .813 | −.2044<br>P = .279 | −.0167<br>P = .930 | .2114<br>P = .262 |
| MBG0  | .0694<br>P = .742 | −.1478<br>P = .481 | .0877<br>P = .677 | .3029<br>P = .141 |
| SBG0  | .3957<br>P = .050 | .1998<br>P = .338 | −.1054<br>P = .616 | −.0813<br>P = .699 |
| LBGI0 | .3954<br>P = .050 | .4970<br>P = .011 | −.0921<br>P = .662 | −.3856<br>P = .057 |
| HBGI0 | .2211<br>P = .288 | .0253<br>P = .904 | .0509<br>P = .809 | .2033<br>P = .330 |
| ADRR0 | .5900<br>P = .002 | .4831<br>P = .014 | −.1222<br>P = .561 | −.5162<br>P = .008 |

Thus, increased glucose variability measured in subjects' natural environment is related to both increased glucose uptake and reduced counterregulatory response measured in a hospital study, a result that will serve as a base for the development of a bolus calculator. No other measure of glucose variability achieved statistically significant relationship with these hospital parameters, which underscores the importance of measuring BG variability in risk space.

(3) The exploratory correlations between SMBG and carb/insulin parameters below show certain dependences between the average BG and LBGI and insulin boluses and between ADRR and insulin basal rate that will be investigated further to design a bolus calculator:

|         | MBG              | SBG              | LBGI             | HBGI             | ADRR             |
|---------|------------------|------------------|------------------|------------------|------------------|
| TOTINS  | −.0940<br>P = .621 | −.2948<br>P = .114 | −.2661<br>P = .155 | −.1741<br>P = .358 | −.3368<br>P = .069 |
| INS_KG  | .0432<br>P = .821 | −.2038<br>P = .280 | −.3137<br>P = .091 | −.0439<br>P = .818 | −.2264<br>P = .229 |
| CARB    | −.5169<br>P = .003 | −.4008<br>P = .028 | .2241<br>P = .234 | −.5171<br>P = .003 | .0753<br>P = .692 |
| BOLUS   | .1247<br>P = .580 | .1185<br>P = .599 | −.2962<br>P = .181 | .0774<br>P = .732 | .0111<br>P = .961 |
| BOLUS1  | .3365<br>P = .126 | .3085<br>P = .162 | −.3745<br>P = .086 | .2887<br>P = .193 | .2218<br>P = .321 |

|        | MBG              | SBG              | LBGI             | HBGI             | ADRR             |
|--------|------------------|------------------|------------------|------------------|------------------|
| BASAL  | .0434<br>P = .848 | −.1794<br>P = .424 | −.2668<br>P = .230 | −.0109<br>P = .962 | −.5108<br>P = .015 |
| BASAL1 | .2699<br>P = .225 | −.0454<br>P = .841 | −.3896<br>P = .073 | .2107<br>P = .347 | −.4380<br>P = .041 |

Example C

Field Glucose Variability Index is Related to Laboratory Measures of Insulin Sensitivity and Hypoglycemia Counterregulation Background and Aims: Contemporary studies increasingly support the idea that blood glucose (BG) variability is a major determinant of diabetes complications; therefore BG variability, along with $HbA_{1c}$, becomes a major marker of glycemic control in Type 1 and Type 2 diabetes (T1DM, T2DM). However, quantifying glucose variability is not straightforward—traditional variability measures, such as standard deviation (SD), M-value, etc. appear to be mostly dependent on hyperglycemic excursions, ignoring hypoglycemic BG fluctuations and being insensitive to hypoglycemia-related characteristics of T1DM.

This study introduces a new variability measure computed from routine self-monitoring BG (SMBG) data, the Average Daily Risk Range (ADRR), which is equally sensitive to hypoglycemic and hyperglycemic excursions, and investigates its relationship with laboratory parameters of glucose dynamics in T1DM.

Materials and Methods: Twenty-five adults with T1DM, average age=42.5±12 years, duration of diabetes=21.6±9.4 years, $HbA_{1c}$=7.4±0.8, 16 males, performed routine SMBG for 2 months, 4-5 times/day. The ADRR was computed from routine SMBG data taking into account the value and the time of each SMBG reading. SD of BG and M-value were computed as well. Subjects were then hospitalized and their BG was controlled overnight at ~6 mmol/l. Hyperinsulinemic clamp (1 mU/kg/minute) was initiated in the morning, beginning with 2-hour euglycemia at ~5.5 mmol/l, followed by 1-hour descent into hypoglycemia with a target level of 2.2 mmol/l. BG was sampled every 5 minutes (YSI); epinephrine was sampled twice at euglycemia and every 10 min during descent in hypoglycemia. Glucose uptake during euglycemia was computed in mg/kg/min as a marker of insulin sensitivity.

Results: Within the field SMBG data the ADRR correlated approximately equally well with significant hypoglycemic (BG≤2.2 mmol/l) and hyperglycemic (BG>22.2 mmol/l) episodes, correlations of r=0.42 and r=0.51 respectively, p<0.05. In contrast, the SD of BG and the M-value had zero correlation with hypoglycemic events and r=0.63, r=0.54 with hyperglycemic events respectively, confirming previous observations that these measures are primarily related to hyperglycemic excursions.

The ADRR, computed from SMBG, was highly predictive of subsequent hospital laboratory results: its correlation with subjects' glucose uptake during euglycemia was 0.59; its correlation with [the logarithm of] peak epinephrine during induced hypoglycemia was −0.59, p=0.002, indicating that the ADRR was equally related to both insulin sensitivity and degree of counterregulation. No other measure of glucose variability achieved statistically significant relationship with these hospital parameters.

Conclusions: A new field glucose variability measure called ADRR that is calculated from regular time-stamped SMBG data, specifically designed to be equally sensitive to hypoglycemia and hyperglycemia, is more closely related to both increased glucose uptake and reduced counterregulatory response than any other measures of variability tested. Further studies will determine whether the active reduction of field glucose variability, as measured by ADRR, will improve counterregulatory response and insulin sensitivity in T1DM.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. A system for enabling a diabetes patient to maintain accurate control over their blood glucose level by determining blood glucose variability, said system comprising:
   an acquisition module acquiring a plurality of blood glucose data points representing glucose concentration levels in blood of said patient;
   a processor programmed to:
      transform the plurality of blood glucose data points received from said acquisition module from a blood glucose range to a transformed range according to a transforming function,
      calculate a risk value for one or more of a plurality of the transformed plurality of blood glucose data points,
      calculate one or more risk ranges each based on a respective one of the calculated risk values within a period of time with a predetermined duration, and
      calculate at least one composite risk range based on one or more of the calculated risk ranges;
   a display module displaying said at least one composite risk range to said patient to prompt said patient, in response to visualization by said patient of said at least one composite risk range, to take a non-hypoglycemia or a non-hyperglycemia action to maintain their blood glucose level within a euglycemic range based on the value of said at least one composite risk range; and
   an audio module to transmit to said patient an audible tone corresponding to a risk of deviation from said euglycemic range based on the value of said at least one composite risk range,
   wherein at least said processor is configured for communication with an insulin delivery device of said patient, and based on the value of said at least one composite risk range indicating hyperglycemia, said processor causes the administration of insulin to said patient via said insulin delivery device.

2. The system of claim 1, wherein the calculation of said at least one
composite risk range comprises computing an average risk range.

3. The system of claim 2, wherein the average risk range is computed as:

$$ADRR = \frac{1}{M}\sum_{i=1}^{M}[LR^i + HR^i],$$

where $LR^i$ represents a maximal hypoglycemic risk value for period of time with a predetermined duration i, $HR^i$ represents a maximal hyperglycemic risk value for period of time with a predetermined duration i, $LR^i + HR^i$ represents a calculated risk range for period of time with predetermined duration i, and the plurality of blood glucose data points are collected on periods of time with predetermined duration i=1, 2, . . . , M.

4. The system of claim 1, wherein the calculation of said composite risk range comprises computing a standard deviation risk range.

5. The system of claim 4, wherein the standard deviation risk range is computed as:

$$SDRR^2 = \frac{1}{M-1}\sum_{i=1}^{M}[(LR^i + HR^i) - \text{mean}(LR^i + HR^i)]^2,$$

where $LR^i$ represents a maximal hypoglycemic risk value for period of time with a predetermined duration i, $HR^i$ represents a maximal hyperglycemic risk value for period of time with a predetermined duration i, $LR^i + HR^i$ represents a calculated risk range for period of time with predetermined duration i, and the plurality of blood glucose data points are collected on periods of time with predetermined duration i=1, 2, . . . , M.

6. The system of claim 1, wherein the plurality of blood glucose data points includes at least three blood glucose data point readings per period of time with predetermined duration.

7. The system of claim 1, wherein the plurality of blood glucose data points includes blood glucose data points from about one to about two weeks of self-monitoring.

8. The system of claim 1, wherein the plurality of blood glucose data points includes blood glucose data points from about two to about six weeks of self-monitoring.

9. The system of claim 8, wherein the plurality of blood glucose data points includes blood glucose data points from about four weeks of self-monitoring.

10. The system of claim 1, wherein the plurality of blood glucose data points includes blood glucose data points from greater than about six weeks of self-monitoring.

11. The system of claim 1, wherein the plurality of blood glucose data points includes about thirty to about seventy-five blood glucose data points.

12. The system of claim 1, wherein the plurality of blood glucose data points includes about seventy-five blood glucose data points.

13. The system of claim 1, wherein the plurality of blood glucose data points includes greater than about seventy-five blood glucose data points.

14. The system of claim 1, wherein the display module comprises a gauge, said gauge having at least one indicator, wherein the at least one indicator displays the calculated composite risk range.

15. The system of claim 14, wherein the gauge is segmented into at least one category including Low Risk, Moderate Risk, and High Risk.

16. The system of claim 15, wherein the Low Risk category corresponds to a composite risk range between about 0 and about 20, the Moderate Risk category corresponds to a composite risk range between about 20 and about 40, and the High Risk category corresponds to a composite risk range greater than about 40.

17. The system of claim 14, wherein the gauge is segmented into at least one category including Low Risk, Low-Moderate Risk, Moderate-High Risk, and High Risk.

18. The system of claim 17, wherein the Low Risk category corresponds to a composite risk range between about 0 and about 20, the Low-Moderate Risk category corresponds to a composite risk range between about 20 and about 30, the Moderate-High Risk category corresponds to a composite risk range between about 30 and about 40, and the High Risk category corresponds to a composite risk range greater than about 40.

19. The system of claim 1, wherein said display module comprises:
a high blood glucose indicator; and
a low blood glucose indicator.

20. The system of claim 1, further comprising a storage module, said storage module storing the calculated composite risk range into a plurality of category levels.

21. The system of claim 1, wherein said display module displays the calculated composite risk range into a plurality of category levels.

22. The system of claim 1 further comprising:
a storage module, said storage module storing the calculated composite risk range into a plurality of category levels; and
wherein said display module displays the calculated composite risk range into a plurality of category levels.

23. The system of claim 1, wherein said display module displays the calculated composite risk range on an analog and/or digital display.

24. The system of claim 1, wherein the period of time with predetermined duration is about daytime or about nighttime in a daytime/nighttime cycle.

25. The system of claim 1, wherein the period of time with predetermined duration is greater than about daytime or about a nighttime in a daytime/nighttime cycle but less than a twenty-four hour period.

26. The system of claim 1, wherein the period of time with predetermined duration is less than a twenty-four hour period.

27. The system of claim 1, wherein the period of time with predetermined duration is about a twenty-four hour period.

28. The system of claim 1, wherein the period of time with predetermined duration is greater than a twenty-four hour period but less than about a week.

29. The system of claim 1, wherein the period of time with predetermined duration is about a week.

30. The system of claim 1, wherein the period of time with predetermined duration is greater than a week.

31. A computer program product comprising a non-transitory computer-readable storage medium having computer-executable instructions stored thereon for enabling a diabetes patient to maintain accurate control over their blood glucose level by enabling at least one processor in a computer system to measure blood glucose variability, said computer-executable instructions comprising instructions causing said processor to:
acquire a plurality of blood glucose data points representing glucose concentration values in blood of said patient;
transform the plurality of blood glucose data points from a blood glucose range to a transformed range according to a transforming function;
calculate a risk value for one or more of a plurality of the transformed plurality of blood glucose data points;
calculate one or more risk ranges each based on a respective one of the calculated risk values within a period of time with a predetermined duration;
calculate at least one composite risk range based on at least on one or more of the calculated risk ranges;
wherein said at least one composite risk range is outputted to said patient via a display thereof to prompt said patient, in response to visualization by said patient of said at least one composite risk range, to take a non-hypoglycemia or a non-hyperglycemia action to maintain their blood glucose level within a euglycemic range based on the value of said at least one composite risk range;
wherein an alert corresponding to a risk of deviation from said euglycemic range based on the value of said at least one composite risk range is generated to be transmitted to said patient as an audible tone, and
wherein said processor is configured for communication with an insulin delivery device of said patient, and based on the value of said at least one composite risk range indicating hyperglycemia, said processor causes the administration of insulin to said patient via said insulin delivery device.

32. The computer program product of claim 31, wherein the calculation of said at least one composite risk range comprises computing an average risk range.

33. The computer program product of claim 32, wherein the average risk range is computed as:

$$ADRR = \frac{1}{M}\sum_{i=1}^{M}[LR^i + HR^i],$$

where $LR^i$ represents a maximal hypoglycemic risk value for period of time with a predetermined duration i, $HR^i$ represents a maximal hyperglycemic risk value for period of time with a predetermined duration i, $LR^i + HR^i$ represents a calculated risk range for period of time with predetermined duration i, and the plurality of blood glucose data points are collected on periods of time with predetermined duration i=1, 2, ..., M.

34. The computer program product of claim 31, wherein the calculation of said composite risk range comprises computing a standard deviation risk range.

35. The computer program product of claim 34, wherein the standard deviation risk range is computed as:

$$SDRR^2 = \frac{1}{M-1}\sum_{i=1}^{M}[(LR^i + HR^i) - \text{mean}(LR^i + HR^i)]^2,$$

where $LR^i$ represents a maximal hypoglycemic risk value for period of time with a predetermined duration i, $HR^i$ represents a maximal hyperglycemic risk value for period of time with a predetermined duration i, $LR^i + HR^i$ represents a calculated risk range for period of time with predetermined duration i, and the plurality of blood glucose data points are collected on periods of time with predetermined duration i=1, 2, ..., M.

36. The computer program product of claim 31, wherein the plurality of blood glucose data points includes at least three blood glucose data point readings per period of time with predetermined duration.

37. The computer program product of claim 36, wherein the plurality of blood glucose data points includes blood glucose data points from about one to about two weeks of self-monitoring.

38. The computer program product of claim 36, wherein the plurality of blood glucose data points includes blood glucose data points from about two to about six weeks of self-monitoring.

39. The computer program product of claim 38, wherein the plurality of blood glucose data points includes blood glucose data points from about four weeks of self-monitoring.

40. The computer program product of claim 31, wherein the plurality of blood glucose data points includes blood glucose data points from greater than about six weeks of self-monitoring.

41. The computer program product of claim 31, wherein the plurality of blood glucose data points includes about thirty to about seventy-five blood glucose data points.

42. The computer program product of claim 31, wherein the plurality of blood glucose data points includes about seventy-five blood glucose data points.

43. The computer program product of claim 31, wherein the plurality of blood glucose data points includes greater than about seventy-five blood glucose data points.

44. The computer program product of claim 41, wherein displaying the calculated composite risk range comprises providing a gauge having at least one indicator, wherein the at least one indicator displays the calculated composite risk range.

45. The computer program product of claim 44, wherein the gauge is segmented into at least one category including Low Risk, Moderate Risk, and High Risk.

46. The computer program product of claim 45, wherein the Low Risk category corresponds to a composite risk range between about 0 and about 20, the Moderate Risk category corresponds to a composite risk range between about 20 and about 40, and the High Risk category corresponds to a composite risk range greater than about 40.

47. The computer program product of claim 44, wherein the gauge is segmented into at least one category including Low Risk, Low-Moderate Risk, Moderate-High Risk, and High Risk.

48. The computer program product of claim 47, wherein the Low Risk category corresponds to a composite risk range between about 0 and about 20, the Low-Moderate Risk category corresponds to a composite risk range between about 20 and about 30, the Moderate-High Risk category corresponds to a composite risk range between about 30 and about 40, and the High Risk category corresponds to a composite risk range greater than about 40.

49. The computer program product of claim 31, wherein said display of the calculated composite risk range comprises:
providing a high blood glucose indicator; and
providing a low blood glucose indicator.

50. The computer program product of claim 31, wherein said computer-executable instructions further comprising causing said processor to store and/or display the calculated composite risk range into a plurality of category levels.

51. The computer program product of claim 31, wherein said computer-executable instructions further comprising instructions causing said processor to display the calculated composite risk range on an analog and/or digital display.

52. The computer program product of claim 31, wherein the period of time with predetermined duration is about daytime or about nighttime in a daytime/nighttime cycle.

53. The computer program product of claim 31, wherein the period of time with predetermined duration is greater than about daytime or about a nighttime in a daytime/nighttime cycle but less than a twenty-four hour period.

54. The computer program product of claim 31, wherein the period of time with predetermined duration is less than a twenty-four hour period.

55. The computer program product of claim 31, wherein the period of time with predetermined duration is about a twenty-four hour period.

56. The computer program product of claim 31, wherein the period of time with predetermined duration is greater than a twenty-four hour period but less than about a week.

57. The computer program product of claim 31, wherein the period of time with predetermined duration is about a week.

58. The computer program product of claim 31, wherein the period of time with predetermined duration is greater than a week.

59. A system for enabling a diabetes patient to maintain accurate control over their blood glucose level by measuring blood glucose variability, said system comprising:

an acquisition module acquiring a plurality of self-monitored blood glucose data points, wherein the plurality of self-monitored blood glucose data points span a period of at least one day;
a processor programmed to:
transform the plurality of self-monitored blood glucose data points from a blood glucose range to a transformed range according to a transforming function, wherein the minimal and maximal values of the transformed range are $-\sqrt{10}$ and $\sqrt{10}$, respectively, wherein the transforming function is:

$$f(BG,\alpha,\beta,\gamma)=\gamma \cdot [(\ln(BG))^\alpha - \beta],$$

where BG is a blood glucose value, $(\alpha,\beta,\gamma)=(1.026, 1.861, 1.794)$ if BG is measured in mM, and $(\alpha,\beta,\gamma)=(1.084, 5.381, 1.509)$ if BG is measured in mg/dl;
define a BG risk space, wherein the BG risk space is:

$$r(BG)=10 \cdot f(BG)^2;$$

define a left branch of the BG risk space representing a risk of hypoglycemia as:

$$rl(BG)=r(BG) \text{ if } f(BG)<0 \text{ and } 0 \text{ otherwise};$$

define a right branch of the BG risk space representing a risk of hyperglycemia as:

$$rh(BG)=r(BG) \text{ if } f(BG)>0 \text{ and } 0 \text{ otherwise};$$

calculate a maximal hypoglycemic risk value for the plurality of self-monitored blood glucose data points for each day as:

$$LR^i = \max(rl(x_1^i), rl(x_2^i), \ldots, rl(x_{n_i}^i)),$$

where $n_i$ is the number of readings for each day i and $x_1^i$, $x_2^i, \ldots, x_{n_i}^i$ are the $n_i$ self-monitored blood glucose data points for each day i;
calculate a maximal hyperglycemic risk value for the plurality of self-monitored blood glucose data points for each day as:

$$HR^i = \max(rh(x_1^i), rh(x_2^i), \ldots, rh(x_{n_i}^i)),$$

where $n_i$ is the number of readings for each day i and $x_1^i$, $x_2^i, \ldots, x_{n_i}^i$ are the $n_i$ self-monitored blood glucose data points for each day i;
calculate an average daily risk range as:

$$ADRR = \frac{1}{M} \sum_{i=1}^{M} [LR^i + HR^i],$$

where the plurality of self-monitored blood glucose data points are collected on days i=1, 2, ..., M;
classify the average daily risk range into one of at least four categories, wherein said at least four categories includes Low, Low-Moderate, Moderate-High, and High, wherein the Low Risk category corresponds to a risk range between about 0 and about 20, the Low-Moderate Risk category corresponds to a risk range between about 20 and about 30, the Moderate-High Risk category corresponds to a risk range between about 30 and about 40; and the High Risk category corresponds to a risk range greater than about 40;
a display module displaying the average daily risk range and the one of the at least four categories into which the average daily risk range is classified to prompt said patient, in response to visualization by said patient of the average daily risk range and the one of the at least four categories into which the average daily risk range is classified, to take a non-hypoglycemia or a non-hyperglycemia action to maintain their blood glucose level within a euglycemic range based on the value of said average daily risk range and the one of the at least four categories; and
an audio module to transmit to said patient an audible tone corresponding to a risk of deviation from said euglycemic range based on the value of said average daily risk range and the one of the at least four categories,
wherein at least said processor is configured for communication with an insulin delivery device of said patient, and based on the value of said average daily risk range and the one of the at least four categories indicating hyperglycemia, said processor causes the administration of insulin to said patient via said insulin delivery device.

60. A computer program product comprising a non-transitory computer-readable storage medium having computer-executable instructions stored thereon for enabling a diabetes patient to maintain accurate control over their blood glucose level by enabling at least one processor in a computer system to measure blood glucose variability, said computer-executable instructions comprising instructions causing said processor to:
acquire a plurality of self-monitored blood glucose data points representing glucose concentration values in blood of said patient, wherein the plurality of self-monitored blood glucose data points span a period of at least one day;
transform the plurality of self-monitored blood glucose data points from a blood glucose range to a transformed range according to a transforming function, wherein the minimal and maximal values of the transformed range are $-\sqrt{10}$ and $\sqrt{10}$, respectively, wherein the transforming function is:

$$f(BG,\alpha,\beta,\gamma)=\gamma \cdot [(\ln(BG))^\alpha - \beta],$$

where BG is a blood glucose value, $(\alpha,\beta,\gamma)=(1.026, 1.861, 1.794)$ if BG is measured in mM, and $(\alpha,\beta,\gamma)=(1.084, 5.381, 1.509)$ if BG is measured in mg/dl;
define a BG risk space, wherein the BG risk space is:

$$r(BG)=10 \cdot f(BG)^2;$$

define a left branch of the BG risk space representing a risk of hypoglycemia as:

$$rl(BG)=r(BG) \text{ if } f(BG)<0 \text{ and } 0 \text{ otherwise};$$

define a right branch of the BG risk space representing a risk of hyperglycemia as:

$$rh(BG)=r(BG) \text{ if } f(BG)>0 \text{ and } 0 \text{ otherwise};$$

calculate a maximal hypoglycemic risk value for the plurality of self-monitored blood glucose data points for each day as:

$$LR^i = \max(rl(x_1^i), rl(x_2^i), \ldots, rl(x_{n_i}^i)),$$

where $n_i$ is the number of readings for each day i and $x_1^i$, $x_2^i, \ldots, x_{n_i}^i$ are the $n_i$ self-monitored blood glucose data points for each day i;
calculate a maximal hyperglycemic risk value for the plurality of self-monitored blood glucose data points for each day as:

$$HR^i = \max(rh(x_1^i), rh(x_2^i), \ldots, rh(x_{n_i}^i)),$$

where $n_i$ is the number of readings for each day i and $x_1^i$, $x_2^i, \ldots, x_{n_i}^i$ are the $n_i$ self-monitored blood glucose data points for each day i;

calculate an average daily risk range as:

$$ADRR = \frac{1}{M}\sum_{i=1}^{M}[LR^i + HR^i],$$

where the plurality of self-monitored blood glucose data points are collected on days i=1, 2, . . . , M;
classify the average daily risk range into one of at least four categories, wherein said at least four categories includes Low, Low-Moderate, Moderate-High, and High, wherein the Low Risk category corresponds to a risk range between about 0 and about 20, the Low-Moderate Risk category corresponds to a risk range between about 20 and about 30, the Moderate-High Risk category corresponds to a risk range between about 30 and about 40; and the High Risk category corresponds to a risk range greater than about 40;
display the average daily risk range and the one of the at least four categories into which the average daily risk range is classified to prompt said patient, in response to visualization by said patient of the average daily risk range and the one of the at least four categories into which the average daily risk range is classified, to take a non-hypoglycemia or a non-hyperglycemia action to maintain their blood glucose level within a euglycemic range based on the value of said average daily risk range and the one of the at least four categories; and
generate an alert corresponding to a risk of deviation from said euglycemic range based on the value of said average daily risk range and the one of the at least four categories as an audible tone,
wherein said processor is configured for communication with an insulin delivery device of said patient, and based on the value of said average daily risk range and the one of the at least four categories indicating hyperglycemia, said processor causes the administration of insulin to said patient via said insulin delivery device.

61. A system for enabling a diabetes patient to maintain accurate control over their blood glucose level by measuring blood glucose variability, said system comprising:
an acquisition module acquiring a plurality of blood glucose data points;
a processor programmed to:
calculate a plurality of risk ranges based on a plurality of blood glucose data points within a period of time with a predetermined duration, and
calculate at least one average predetermined duration blood glucose risk range based on a plurality of calculated risk ranges;
a display module displaying said at least one average predetermined duration blood glucose risk range to said patient to prompt said patient, in response to visualization by said patient of said at least one average predetermined duration blood glucose risk range to take a non-hypoglycemia or a non-hyperglycemia action to maintain their blood glucose level within a euglycemic range based on the value of said at least one average predetermined duration blood glucose risk range; and
an audio module to transmit to said patient an audible tone corresponding to a risk of deviation from said euglycemic range based on the value of said at least one average predetermined duration blood glucose risk range,
wherein at least said processor is configured for communication with an insulin delivery device of said patient, and based on the value of said at least one average predetermined duration blood glucose risk range indicating hyperglycemia, said processor causes the administration of insulin to said patient via said insulin delivery device.

62. The system of claim 61, wherein predetermined duration is a day whereby said at least one average predetermined duration blood glucose risk range provides an average daily blood glucose risk range.

63. The system of claim 62, wherein the average daily blood glucose risk range is calculated as:
$BGRANGE = 1/M\Sigma_{i=1}^{M}[\max_{j=1,ni}(x_j^i) - \min_{j=1,ni}(x_j^i)]$
where $n_i$ is the number of readings for each day i, $x_j^i$ is the jth blood glucose data point for day i, $\max_{j=1,ni}(x_j^i) - \min_{j=1,ni}(x_j^i)]$ represents a calculated daily risk range for day i, and the plurality of blood glucose data point are collected on days i=1, 2, . . . , M.

64. A computer program product comprising a non-transitory computer-readable storage medium having computer-executable instructions stored thereon for enabling a diabetes patient to maintain accurate control over their blood glucose level by enabling at least one processor in a computer system to measure blood glucose variability, said computer-executable instructions comprising instructions causing said processor to:
acquire a plurality of blood glucose data points;
calculate at least one risk range based on at least two of the plurality of blood glucose data points; and
calculate at least one average daily blood glucose risk range based on at least one of the calculated daily risk ranges;
wherein said at least one average daily blood glucose risk range is outputted to said patient via a display thereof to prompt said patient, in response to visualization by said patient of said at least one average daily blood glucose risk range, to take a non-hypoglycemic or a non-hyperglycemic action to maintain their blood glucose level within a euglycemic range based on the value of said at least one average daily blood glucose risk range;
wherein an alert corresponding to a risk of deviation from said euglycemic range based on the value of said at least one average daily blood glucose risk range is generated to be transmitted to said patient as an audible tone,
wherein said processor is configured for communication with an insulin delivery device of said patient, and based on the value of said at least one average daily blood glucose risk range indicating hyperglycemia, said processor causes the administration of insulin to said patient via said insulin delivery device.

65. The computer program product of claim 64, wherein predetermined duration is a day whereby said at least one average predetermined duration blood glucose risk range provides an average daily blood glucose risk range.

66. The computer program product of claim 65, wherein the average daily blood glucose risk range is calculated as:
$BGRANGE = 1/M\Sigma_{i=1}^{M}[\max_{j=1,ni}(x_j^i) - \min_{j=1,ni}(x_j^i)]$
where $n_i$ is the number of readings for each day i, $x_j^i$ is the jth blood glucose data point for day i, $\max_{j=1,ni}(x_j^i) - \min_{j=1,ni}(x_j^i)]$ represents a calculated daily risk range for day i, and the plurality of blood glucose data point are collected on days i=1, 2, . . . , M.

* * * * *